(12) United States Patent
Porrello et al.

(10) Patent No.: US 11,920,158 B2
(45) Date of Patent: Mar. 5, 2024

(54) CARDIOMYOCYTE MATURATION

(71) Applicant: The Council of the Queensland Institute of Medical Research, Herston (AU)

(72) Inventors: Enzo Porrello, St. Lucia (AU); James Hudson, St. Lucia (AU); Drew Titmarsh, St. Lucia (AU); Richard Mills, St. Lucia (AU)

(73) Assignee: THE COUNCIL OF THE QUEENSLAND INSTITUTE OF MEDICAL RESEARCH, Herston (AU)

( * ) Notice: Subject to any disclaimer, the term of this patent is extended or adjusted under 35 U.S.C. 154(b) by 855 days.

(21) Appl. No.: 16/327,355

(22) PCT Filed: Aug. 25, 2017

(86) PCT No.: PCT/AU2017/050905
§ 371 (c)(1),
(2) Date: Feb. 22, 2019

(87) PCT Pub. No.: WO2018/035574
PCT Pub. Date: Mar. 1, 2018

(65) Prior Publication Data
US 2019/0203179 A1    Jul. 4, 2019

(30) Foreign Application Priority Data

Aug. 26, 2016   (AU) ................... 2016903404

(51) Int. Cl.
| | | |
|---|---|---|
| *C12N 5/077* | (2010.01) | |
| *C12M 1/32* | (2006.01) | |
| *C12M 1/34* | (2006.01) | |
| *C12Q 1/02* | (2006.01) | |

(52) U.S. Cl.
CPC .......... *C12N 5/0657* (2013.01); *C12M 23/12* (2013.01); *C12M 41/00* (2013.01); *C12Q 1/025* (2013.01); *C12N 2500/16* (2013.01); *C12N 2500/34* (2013.01); *C12N 2500/36* (2013.01); *C12N 2500/38* (2013.01); *C12N 2501/115* (2013.01); *C12N 2501/155* (2013.01); *C12N 2501/16* (2013.01); *C12N 2501/999* (2013.01); *C12N 2503/02* (2013.01); *C12N 2506/02* (2013.01); *C12N 2513/00* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 4,999,376 A | * | 3/1991 | Liu ..................... | A61K 36/537 514/738 |
| 2013/0029368 A1 | | 1/2013 | Kattman et al. | |
| 2016/0201034 A1 | | 7/2016 | Zimmermann et al. | |

FOREIGN PATENT DOCUMENTS

| | | |
|---|---|---|
| WO | WO 2014/200339 A1 | 12/2014 |
| WO | WO 2015/187023 A1 | 12/2015 |

OTHER PUBLICATIONS

Rodriguez, Marita; et al; "Measuring the Contractile Forces of Human Induced Pluripotent Stem Cell-Derived Cardiomyocytes With Arrays" Journal of Biomedical Engineering, 136, 1-10, 2014 (Year: 2014).*
Bakunts, Karina; et al; "Formation of cardiac fibers in Matrigel matrix" Biotechniques, 44, 341-346, 2008 (Year: 2008).*
Hashimoto, Sam; Dayton, Seymour; "Utilization of Glucose, Octanoate and Palmitate by Normal Rat Aorta, and the Effect of these Acids and of Albumin on Glucose Metabolism" Proceedings of the Society for Experimental Biology and Medicine, 129, 35-51, 1968 (Year: 1968).*
International Bureau, International Search Report and Written Opinion in International Application No. PCT/AU2017/050905, dated Nov. 9, 2017.
Tan et al., "Cells lying on a bed of microneedles: An approach to isolate mechanical force," PNAS, 100(4): 1484-1489 (2003).
Chen et al., "NS21: Re-defined and Modified Supplemental B27 for Neuronal Cultures", Journal of Neuroscience Methods, 171(2): 239-247 (2008).
Van Der Lee et al., "Effects of fatty acids on uncoupling protein-2 expression in the rat heart", The FASEB Journal, 14: 495-502 (2000).

* cited by examiner

*Primary Examiner* — David W Berke-Schlessel
(74) *Attorney, Agent, or Firm* — Leydig, Voit & Mayer, Ltd.

(57) ABSTRACT

A cardiomyocyte maturation medium comprises a base medium, one or more fatty acids such as palmitic acid, glucose and albumin. The one or more fatty acids and glucose are ideally present at a concentration ratio of about 1:10. Typically, the medium does not comprise TGF or insulin, or comprises minimal TGF and/or insulin. A cell culture vessel is provided that comprises opposed poles that facilitate force measurements of developing cardiac muscle.

19 Claims, 18 Drawing Sheets

Specification includes a Sequence Listing.

CARDIOMYOCYTE MATURATION

CROSS-REFERENCE TO RELATED APPLICATIONS

This patent application is the U.S. national stage of PCT/AU2017/050905, filed Aug. 25, 2017, which claims the benefit of Australian Patent Application No. 2016903404, filed Aug. 26, 2016, each of which is incorporated by reference in its entirety herein.

TECHNICAL FIELD

THIS INVENTION relates to cardiomyocytes. More particularly, this invention relates to a culture medium, system and method that promotes cardiomyocyte maturation in vitro.

BACKGROUND

Maturation of cardiomyocytes occurs during early postnatal life and imposes numerous adaptations including electrophysiological, structural and metabolic changes (1), which occur coincident with loss of proliferative capacity and regenerative potential (2, 3). The discovery of key upstream drivers of cardiomyocyte maturation and cell cycle arrest remains one of the most important unanswered questions in cardiac biology. Discovery of these drivers would facilitate current attempts to promote cardiomyocyte maturation in vitro for drug discovery and to de-differentiate adult cardiomyocytes in vivo for regenerative medicine.

There are considerable changes in metabolic substrate provision during early postnatal life. The mammalian heart relies on high concentrations of carbohydrates and the presence of insulin in utero, but later switches to fatty acid dominated substrates present in milk and low insulin levels post-birth (4). In order to adapt to these changes in substrates, cardiomyocytes upregulate the genes required for fatty acid oxidation after birth (5). The importance of these metabolic adaptations for cardiomyocyte maturation has been difficult to study because genetic disruption of fatty acid oxidation components in vivo can have a broad range of negative health impacts (6). Therefore, there is a need to develop alternative approaches for studying the impact of cardiomyocyte metabolism on the maturation process.

hPSCs are now widely used for the generation of defined human somatic cell types, including cardiomyocytes. hPSC-CMs have been used extensively for developmental studies, drug screening, disease modeling, and heart repair. However, lack of maturity and inappropriate responses to pharmacological agents have been identified as limitations in 2D or embryoid body based differentiation strategies (7). In an effort to better simulate heart muscle structure and function, cardiac tissue engineering to form 3D engineered heart muscle has been used (8-12). These recent advances in human cardiac tissue engineering have greatly enhanced structural and functional maturation of hPSC-CMs. However, metabolic, transcriptional and proliferative maturation have not yet been achieved.

SUMMARY

The invention is broadly directed to a medium having defined constituents that promote or enhance cardiomyocyte maturation. The invention is also broadly directed to a culture system that comprises one or a plurality of wells that facilitate the formation of cardiomyocytes and/or cardiac organoids comprising cardiomyocytes in the aforementioned medium.

A first aspect of the invention provides a cardiac cell maturation medium comprising a base medium, one or more fatty acids, glucose and albumin.

Suitably, the cardiac cell maturation medium is suitable for maturation of cardiomyocytes.

The cardiac cell maturation medium may further comprise a gelling medium that comprises one or more extracellular matrix (ECM) molecules or components thereof.

The one or more extracellular matrix (ECM) molecules or components may be, or comprise, Matrigel™. Preferably, the one or more extracellular matrix (ECM) molecules or components comprises collagen.

Preferably, the one or more fatty acids and glucose are present at a concentration ratio of about 1:10.

Preferably, the one or more fatty acids are, or comprise, palmitic acid.

Suitably, the cardiac cell maturation medium does not comprise TGF or insulin, or comprises minimal TGF or insulin.

Typically, the cardiac cell maturation medium is a serum-free medium.

A second aspect of the invention provides a cardiac cell culture vessel comprising a plurality of wells that each comprise opposed poles that extend substantially perpendicularly from a basal surface of the well.

A third aspect of the invention provides a cardiac cell maturation system comprising:
  (i) the cardiac cell maturation medium of the first aspect; and
  (ii) the cardiac cell culture vessel of the second aspect.

In a particular embodiment, the cardiac cell culture system may be, or is a component of, a heart dynamometer.

A fourth aspect of the invention provides a method of culturing cardiac cells, said method including the step of contacting one or more cardiomyocytes with the cardiac cell maturation medium of the first aspect for sufficient time and under suitable conditions to induce or promote maturation of one or a plurality of cardiomyocytes.

In some embodiments, the one or more cardiomyocytes have been differentiated from one or more progenitor cells. The progenitor cells may be, or comprise, human embryonic stem cells or induced pluripotent stem cells.

In a preferred embodiment, the method is at least partly performed using the cardiac cell maturation system of the third aspect.

Also provided is a cardiac cell, organoid or engineered heart tissue produced by the method of this aspect.

A fifth aspect of the invention provides a method of identifying one or more molecules that modulate cardiac cell maturation, said method including contacting one or more cardiomyocytes with one or more candidate molecules in the cardiac cell maturation system of the second aspect, whereby modification of the maturation of one or a plurality of the cardiomyocytes indicates that the candidate molecule is a modulator of cardiac cell maturation.

In one embodiment, the modulator at least partly inhibits or suppresses cardiomyocyte maturation.

In another embodiment, the modulator at least partly enhances or promotes cardiomyocyte maturation.

A sixth aspect of the invention provides a method of determining, assessing or monitoring the effect of one or more molecules upon a cardiac cell, tissue or organoid, said method including the steps of contacting the cardiac cell, organoid or engineered heart tissue produced according to the method of the third aspect to the one or more molecules and determining, assessing or monitoring the effect of the one or more molecules upon the cardiac cell, organoid or engineered heart tissue.

In particular embodiments, the method determines, assesses or monitors the therapeutic efficacy, safety or toxicity of the one or more molecules.

Data is mean±s.e.m. for the heat maps (f,g,i,j). *$P<0.05$, $P<0.01$, *$P<0.001$, ****$P<0.0001$, using one-way ANOVA with Tukey's post-test (h), with Dunnet's post-test relative to 5.5 mM glucose and no palmitate (f,g,i,j), or t-test (k). # indicates p=0.07 using one-way ANOVA with Dunnet's post-test relative to 5.5 mM glucose and no palmitate (j).

Figure 2:
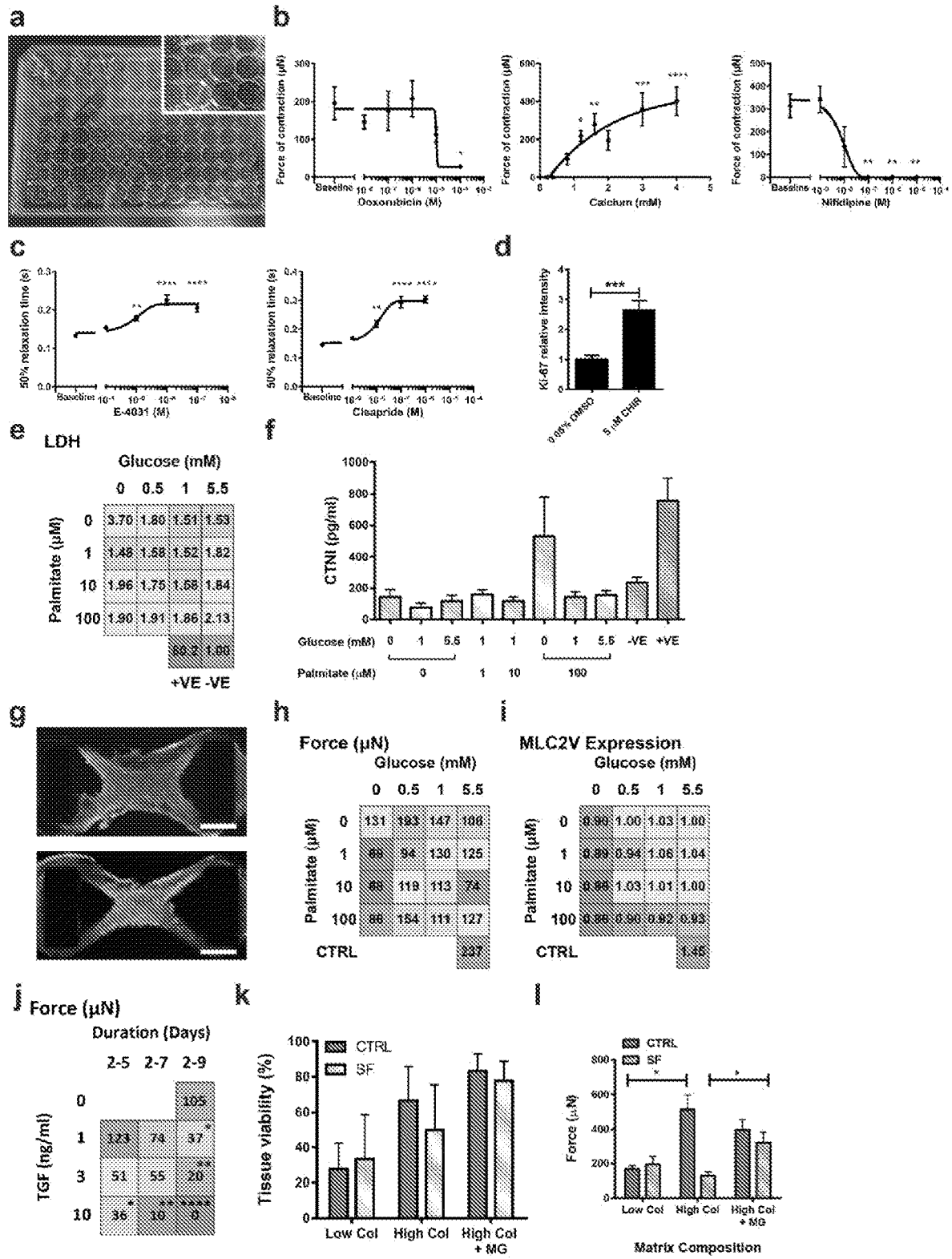

FIG. 2: Development, optimization and characterization of Heart-Dyno.
- a) Photo micrographs of Heart-Dyno culture inserts with hCO in a 96-well plate.
- b) Force of contraction responses to known repressors/activators of force of contraction. n=5.
- c) Pro-arrhythmogenic compounds cause prolonged relaxation time in hCO as expected. n=5.
- d) Validation of Ki-67 marker activation using whole-mount immunostaining. n=5-7 from 2 experiments. hCOs treated with 0.05% DMSO and 5 μm CHIR.
- e) Lactate dehydrogenase (LDH) levels in response to a full-factorial glucose (0, 0.5, 1 & 5.5 mM) and palmitate (0, 1, 10 & 100 μM) screen in the presence of insulin. LDH levels were assessed after 5 days of serum-free culture following 2 days of hCO formation in CTRL medium. n=8-9 from 3 experiments, HES3-derived hCOs. +VE-positive control, −VE-negative control.
- f) Cardiac troponin (CTNI) levels for serum-free conditions. CTNI levels were assessed after 5 days of serum-free culture following 2 days of hCO formation in CTRL medium. n=2-3 from 1 experiment, HES3 ESC line. +VE-positive control, −VE-negative control.
- g) Whole-mount images of hCOs stained with α-actinin that mechanically failed from broken 'arms' (top) and necking (bottom) issues after 5 days of serum-free culture following 2 days of hCO formation in CTRL medium. Scale bars=200 μm.
- h) Force heat-map in response to a full-factorial glucose (0, 0.5, 1 and 5.5 mM) and palmitate (0,1,10 and 100

μM) screen. Force was assessed after 5 days of serum-free culture following 2 days of hCO formation in CTRL medium. n=8-12 tissues from 3 experiments, H9-derived hCOs.

i) Whole-mount MLC2V expression in response to a full-factorial glucose (0, 0.5, 1 and 5.5 mM) and palmitate (0, 1, 10 and 100 μM) screen. MLC2V expression was assessed after 5 days of serum free culture following 2 days of hCO formation in CTRL medium. n=8-12 from 3 experiments, H9-derived hCOs. MLC2V expression is relative to control serum-free conditions (5.5 mM glucose, no palmitate).

j) TGF-β1 is detrimental to hCO function. Force heat-map in response to TGF-01 concentration (0, 1, 3 and 10 ng/ml) and duration (day 2-5, 2-7 and 2-9). Force was assessed after 10 days of serum-free culture following 2 days of hCO formation in CTRL medium. n=13-16 from 3 experiments, H9-derived hCOs.

k) Increased collagen I and Matrigel improve tissue viability. Tissue viability was assessed after 10 days of serum-free culture following 2 days of hCO formation in CTRL medium. n=18 from 3 experiments, H9-derived hCOs. Low Col=1.6 mg/ml collagen matrix, High Col=3.2 mg/ml collagen matrix, High Col+MG=2.6 mg/ml collagen plus 9% (v/v) Matrigel matrix. CTRL=control medium, SF=Serum-free medium (1 mM Glucose, 10 μM Palmitate with insulin).

l) Influence of the amount and composition of extracellular matrix on the force of hCO. Tissue viability was assessed after 10 days of serum free culture following 2 days of hCO formation in CTRL medium. n=6-15 from 3 experiments, H9-derived hCOs. Low Col=1.6 mg/ml collagen matrix, High Col=3.2 mg/ml collagen matrix, High Col+MG-2.6 mg/ml collagen plus 9% (v/v) Matrigel matrix. CTRL—control medium, SF—serum-free medium (1 mM glucose, 10 μM palmitate with insulin).

Data is mean±s.e.m. *P<0.05, P<0.01, *P<0.001, ****P<0.0001, one-way ANOVA plus Dunnet's post-test relative to baseline or 0.2 mM $Ca^{2+}$ (b,c), t-test (d) with Dunnet's post-test relative to no TGF-β1(j) using ANOVA comparing either CTRL medium or SF groups only with Tukey's post-test (1).

Figure 3:
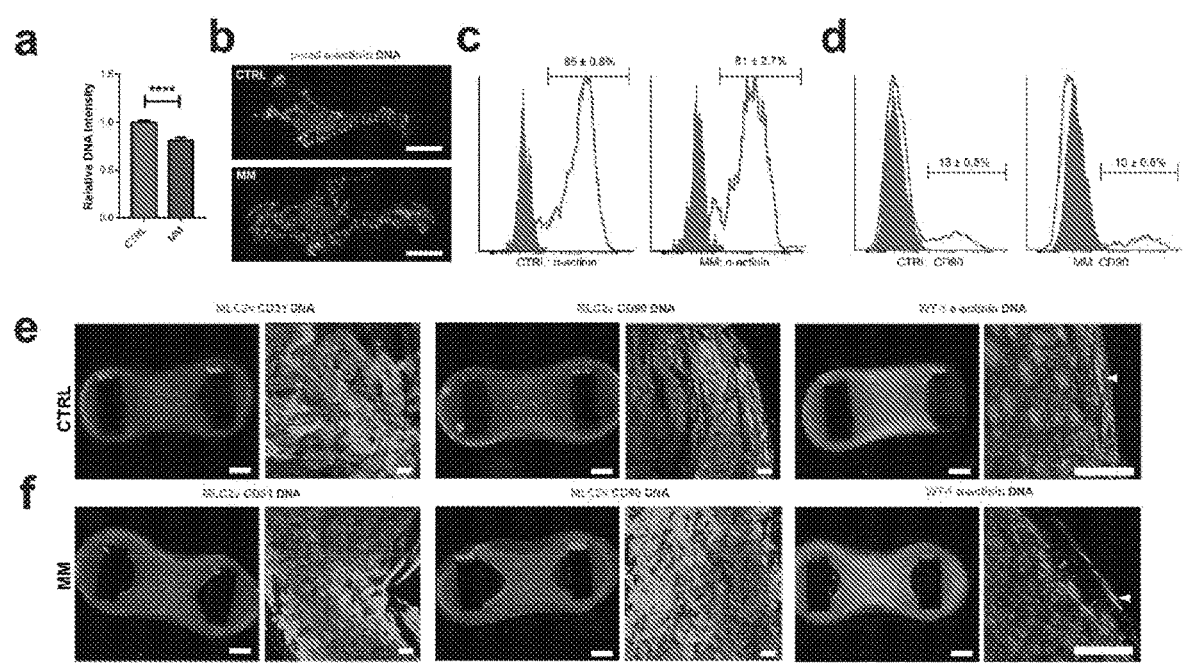

FIG. 3: Culture of hCO in MM does not alter cellular composition.

a) DNA intensity in hCO indicates fewer cells in MM. n=70-74 from 14 experiments.

b) Single hPSC-CMs dissociated from hCO (bars=10 μm).

c) Flow cytometry profiling of hPSC-CMs (α-actinin) dissociated from hCO revels a similar purity in both CTRL medium and MM (not significant).

d) Flow cytometry profiling of stromal cells (CD90+) dissociated from hCO revels a very modest decrease in CD90+ cells in hCO cultured in MM versus CTRL medium (p<0.05). n=5.

e) CTRL medium hCO have endothelial tubular structures (CD31) and stromal cells (CD90) present through the hPSC-CMs (MLC2v). There are also epicardial cells (WT-1) present on the outer surface of the hCO. Low magnification images of the entire hCO are shown on left for each stain (bars=200 μm) and high magnification images are shown on right (bars=20 μm).

f) MM hCO have endothelial tubular structures (CD31) and stromal cells (CD90) present through the hPSC-CMs (MLC2v). There are also epicardial cells (WT-1) present on the outer surface of the hCO. Low magnification of the entire hCO are shown on left for each stain (bars=200 μm) and high magnification are shown on right (bars=20 μm).

Data is presented as mean±S.E.M. *** P<0.001, using t-test (a), statistics analysed using t-test (c,d).

Figure 4:
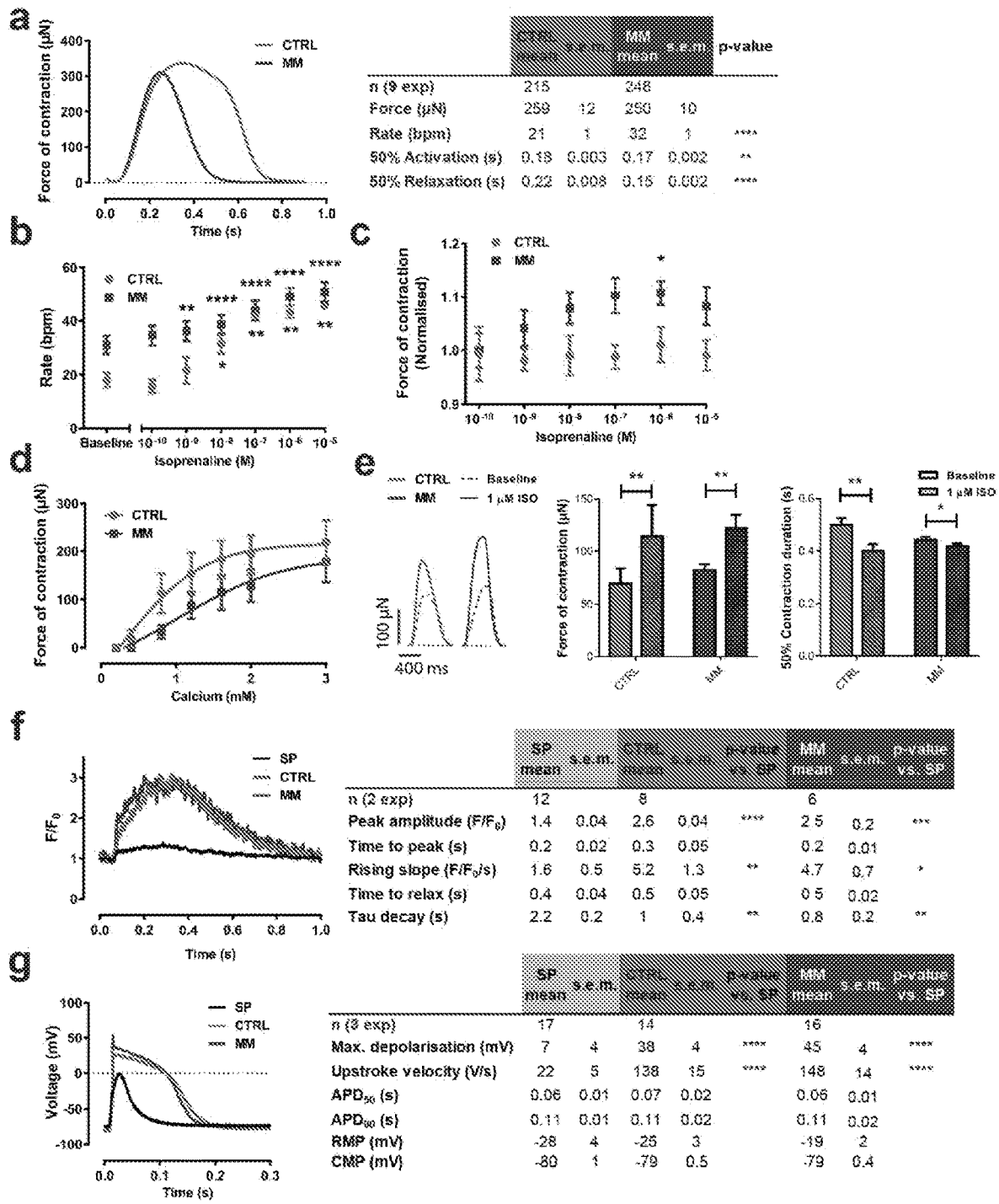

FIG. 4: Maturation of electrophysiological and contractile properties are determined by the tissue-engineered environment.

a) Representative individual contraction curves and contraction parameters of hCOs in CTRL medium or MM.

b) Isoprenaline stimulation induces an increased rate of contraction in hCOs. n=5-6.

c) Isoprenaline increases the force of contraction in hCOs cultured in MM. n=5-7 from 2 experiments.

d) hCOs cultured in MM have decreased calcium sensitivity. As isoprenaline stimulation experiments were performed in culture medium ($Ca^{2+}$=1.8 mM), the effects of isoprenaline may be more pronounced at lower calcium concentrations. n=4-7 from 2 experiments.

e) Isoprenaline increases force of contraction and decreases contraction duration under paced conditions (1 Hz) at the calcium $EC_{50}$ concentrations (CTRL=0.3 mM, MM=1.0 mM). n=7.

f) Representative individual calcium indicator (Fluo-4) recordings and parameters from individual hPSC-CMs dissociated from hCOs cultured in CTRL medium or MM paced at 1 Hz at 37° C.

g) Representative individual action potential recordings and parameters from individual hPSC-CMs dissociated from hCOs cultured in CTRL medium or MM paced at 1 Hz at 37° C. APD—Action Potential Duration, RMP—Resting Membrane Potential, CMP—Clamped Membrane Potential.

Data is mean±s.e.m. *P<0.05, P<0.01, *P<0.001, ****P<0.0001, using t-test (a,e), two-way ANOVA and indicate difference relative to baseline (b,c), ANOVA with Tukey's post-test (f,g). The response curves to calcium of hCO in CTRL medium and MM are statistically significant using two-way ANOVA (p<0.05) (d).

Figure 5:
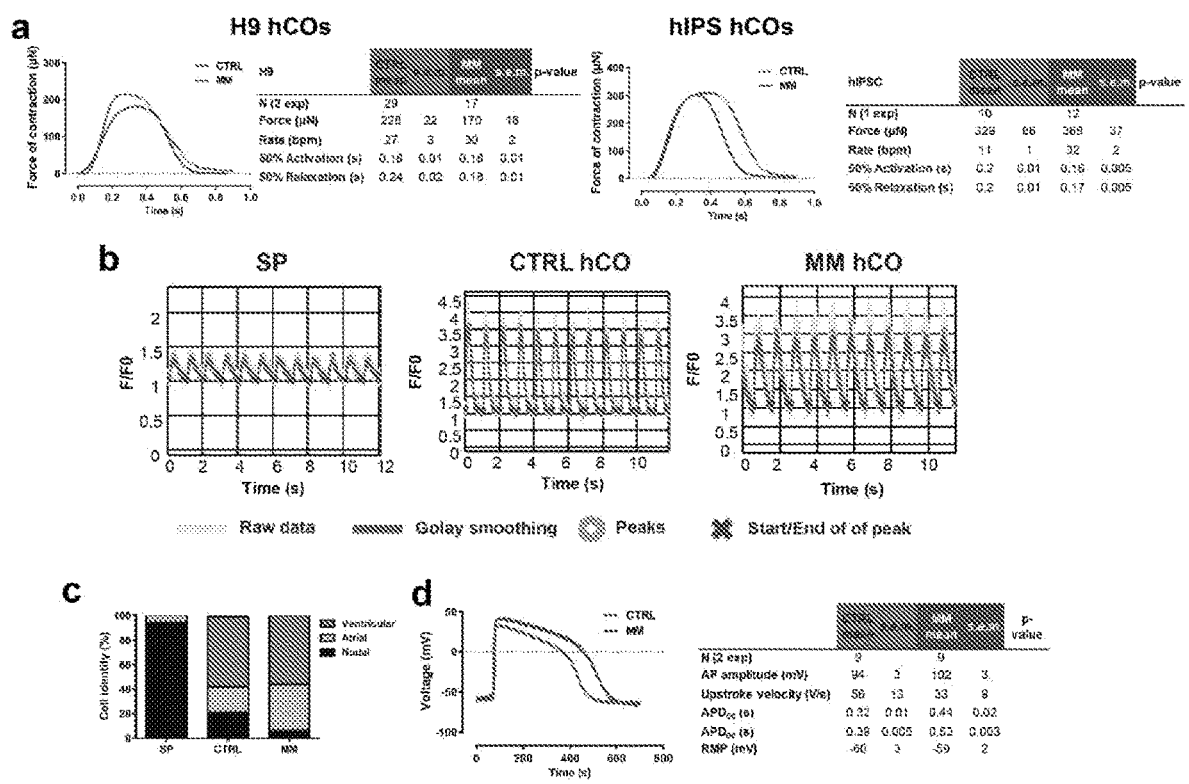

FIG. 5: Supporting data for functional analysis presented in FIG. 4.

a) H9- and iPSC-derived hCOs have similar contraction properties as HES3 hCOs cultured in MM. Representative contraction curves and parameters of H9- or IPSC-derived hCOs in CTRL medium or MM.

b) Raw and processed data of representative calcium traces recorded from hPSC-CMs isolated from 2D culture and hCOs cultured in CTRL medium and MM with Fluo-4 AM at 1 Hz pacing at 37° C.

c) Characterization of hPSC-CM sub-type using patch-clamp (for more detail refer to Materials & Methods).

d) Electrophysiological recordings using impaling electrodes. AP—Action Potential, APD—Action Potential Duration, RMP—Resting Membrane Potential.

Data is mean±s.e.m. *P<0.05, using t-test (d).

Figure 6:
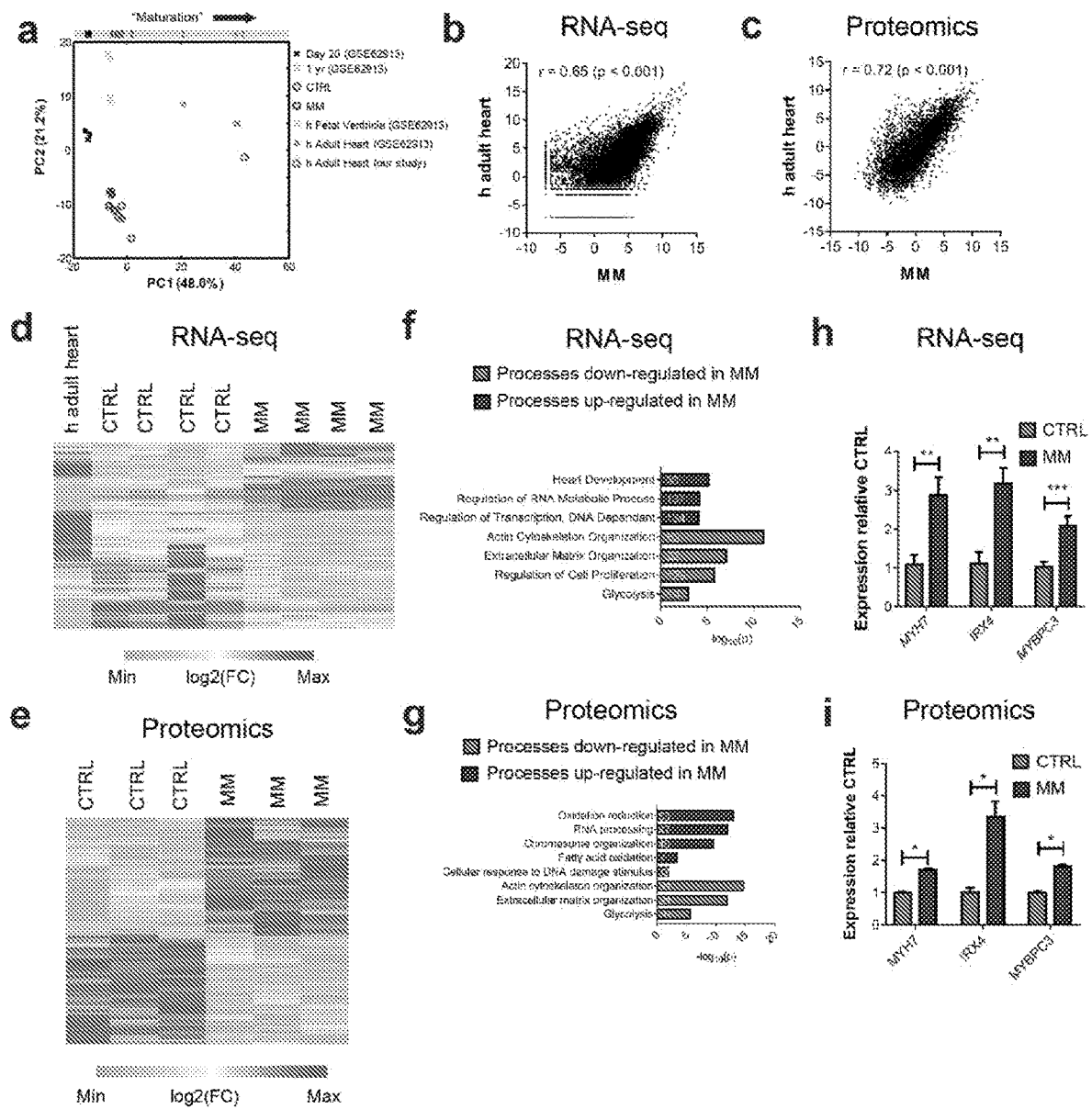

FIG. 6: Culture in MM induces transcriptional and proteomic maturation in hCOs.

a) Principal component analysis of RNA-seq data using a subset of genes identified by Delaughter et al., (27) to profile maturity (genes from Table S6 (27)). RNA-seq data derived from hCOs cultured in CTRL medium or MM (n=4 experiments, each 20 pooled hCOs) and our human adult heart sample (n=1, 3 pooled hearts), combined with RNA-seq data from (GSE62913) (25), containing 2D hPSC-CM at 20 days (n=3), 1 year (n=3), human fetal ventricles (n=2), and human adult hearts (n=2). All genes were >10 counts per million for at least 1 sample. Bar at top is a projection of PC1, the component that correlates with maturation.
b) Pearson correlation co-efficient indicates that hCOs cultured in MM are significantly correlated to human adult heart tissue. Graph is of $\log_2$(CPM) of human adult heart (n=1, 3 pooled hearts) or average gene expression of hCOs cultured in MM (n=4).
c) Pearson correlation co-efficient indicates that hCOs cultured in MM are significantly correlated to human adult heart tissue. Graph is of $\log_2$(iBAQ) of human adult heart (n=1) or pooled hCOs cultured in MM (n=3, each 9 pooled hCO).
d) Clustered heat-map of genes regulated (FDR<0.05) between hCOs cultured in CTRL medium vs MM.
e) Clustered heat-map of proteins regulated (q-value<0.05) between hCOs cultured in CTRL vs MM.
f) GO-term analysis of RNA-seq reveals that multiple processes are decreased or increased in hCOs cultured in MM vs CTRL medium. These are consistent with processes that occur during postnatal heart maturation (5). Numbers in the bars indicate number of genes identified in that particular process.
g) GO-term analysis of proteomics reveals multiple processes are decreased and increased in hCOs cultured in MM vs CTRL medium. These are consistent with processes that occur during postnatal heart maturation (5). Numbers in the bars indicate number of genes identified in that particular process.
h) RNA-seq markers of maturation: genes in the "Cardiac Development" GO-term which are also up-regulated in proteomics data.
i) Proteomics markers of maturation: genes in the "Cardiac Development" GO-term which are also up-regulated in proteomics data.

Data is mean±s.e.m. *P<0.05, *P<0.01,***P<0.001, FDR (h) or q-value (1) for statistical analysis please see Materials & methods.

Figure 7:
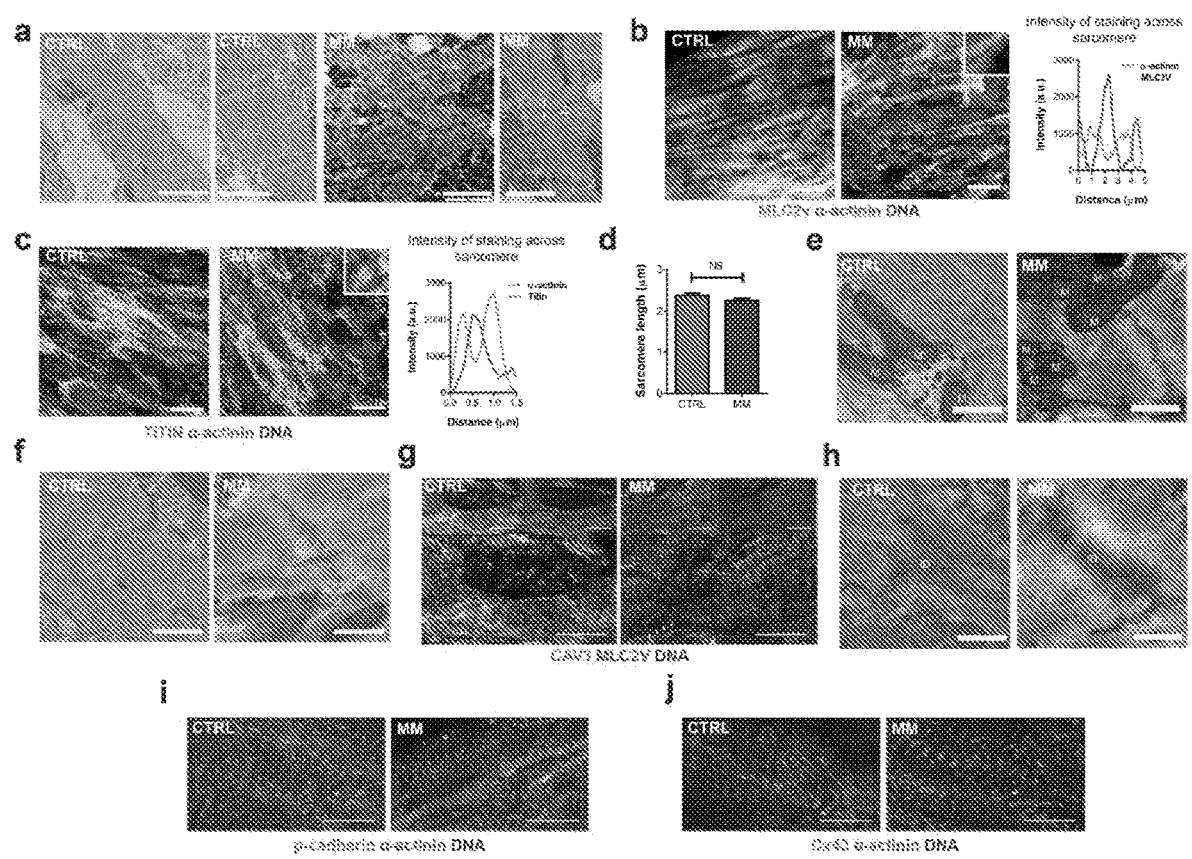

FIG. 7: hCOs cultured in both CTRL medium or MM exhibit in vivo-like structure.
a) Transmission electron micrographs of CTRL medium and MM hCOs for an overview (scale bars=2 μm) and higher focus on sarcomeres (scale bars=1 μm). Z, I-Z and I bands respectively
b) Whole-mount immunostaining of MLC2v and α-actinin reveals the presence of well-developed sarcomeres in hCOs in both CTRL medium and MM (bars=20 μm). Note the 5× inset and intensity profiles, where the MLC2v/α-actinin co-staining reveals α-actinin in the Z-bands and MLC2V only in the rest of the sarcomeres.
c) Whole-mount immunostaining of titin and α-actinin reveals the clear delineation of α-actinin in the Z-bands and titin in the I bands (scale bars=20 μm). Note the 5× inset and intensity profiles, where the titin/α-actinin co-staining reveals α-actinin in the Z-bands and titin only in the I-bands.
d) Quantification of sarcomere length using α-actinin staining. n=20 cells from 2 experiments. Data is mean±s.e.m., NS—not significant using t-test (P<0.05).
e) Transmission electron micrographs of mitochondria (M) in CTRL medium and MM hCOs M—Mitochondria (scale bars=0.5 μm).
f) Transmission electron micrographs of t-tubules (T) in CTRL medium and MM hCOs (scale bars=0.5 μm).
g) Whole-mount immunostaining of CAV3 confirms t-tubule structures in hCO in CTRL medium and MM (scale bars=10 μm).
h) Transmission electron micrographs of intercalated discs (ID) in CTRL medium and MM hCOs (scale bars=0.5 μm).
i) Whole-mount immunostaining of pan-cadherin confirms presence of intercalated discs in hCO in CTRL medium and MM (scale bars=10 μm).
j) Whole-mount immunostaining of connexin 43 confirms presence of intercalated discs in hCO in CTRL medium and MM (scale bars=10 μm).

Figure 8:
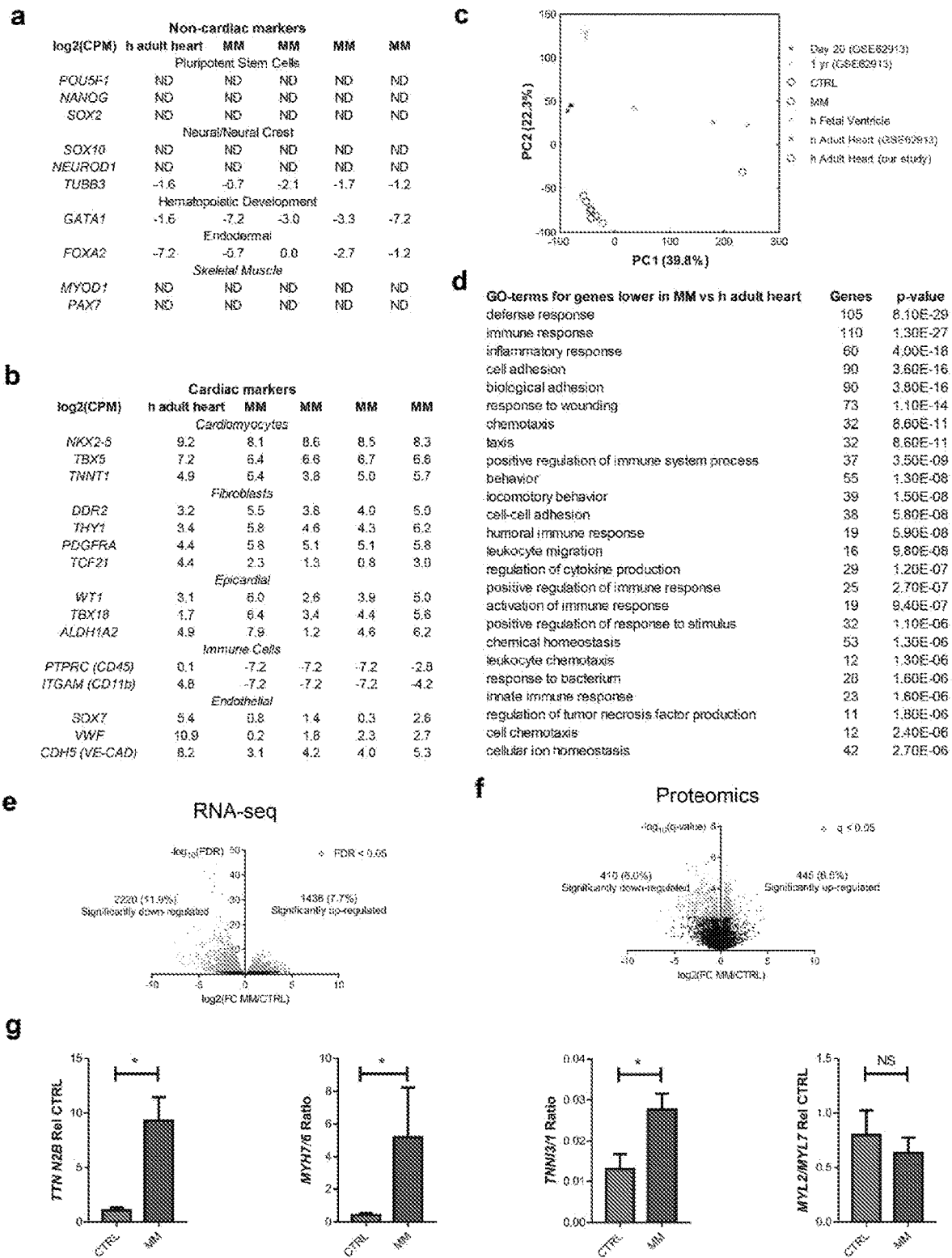

FIG. 8: Supporting data for the RNA-seq and proteomic expression analysis of hCOs presented in FIG. 6.
a) RNA-seq expression of markers for potentially contaminating cell types. n=4 experiments.
b) RNA-seq expression of markers expressed in different cardiac cell populations. n=4 experiments.
c) Principle component analysis of our RNA-seq data combined with RNA-seq data from (GSE62913) (25), containing hPSC-derived 2D hPSC-CMs at 20 days (n=3), 1 year (n=3), human fetal ventricles (n=2), and human adult hearts (n=2). All genes were >10 counts per million for at least 1 sample.
d) Top 25 GO terms for the 1000 genes with highest differential expression between hCOs in MM and human adult heart that are more abundant in the human adult heart.
e) Volcano plot illustrating the differential analysis of the RNA-seq data. n=4 experiments.
f) Volcano plot illustrating the differential analysis of the proteomic data. n=3 samples.
g) qPCR of sarcomeric genes known to switch/increase with maturation (TTN N2B, MYH7/6, TNNI3/1, and MYL2/7). n=4 experiments.

Data is mean (a,b) or mean±s.e.m. (f). *P<0.05, using Mann-Whitney (f).

Figure 9:
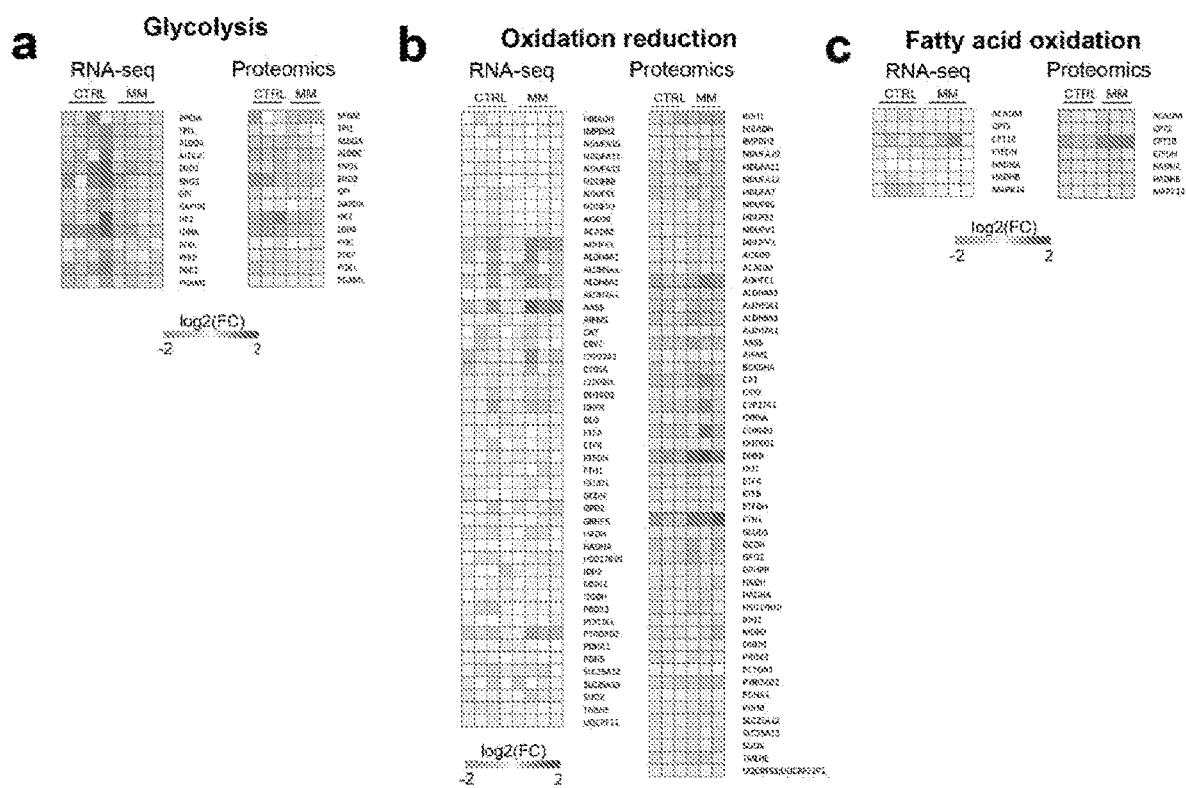

FIG. 9: Heat-maps of RNA-seq and proteomic data for metabolism genes supporting the data presented in FIG. 4.
a) Heat map data from significantly regulated targets (CTRL medium vs MM) in RNA-seq or proteomics data for the GO term "glycolysis"
b) Heat map data from significantly regulated targets (CTRL medium vs MM) in RNA-seq or proteomics data for the GO term "oxidation reduction"
c) Heat map data from significantly regulated targets (CTRL medium vs MM) in RNA-seq or proteomics data for the GO term "fatty acid oxidation"

Data is presented as $\log_2$ expression relative to mean for all conditions. n=4 experiments for RNA-seq and n=3 experiments for proteomics.

Figure 10:
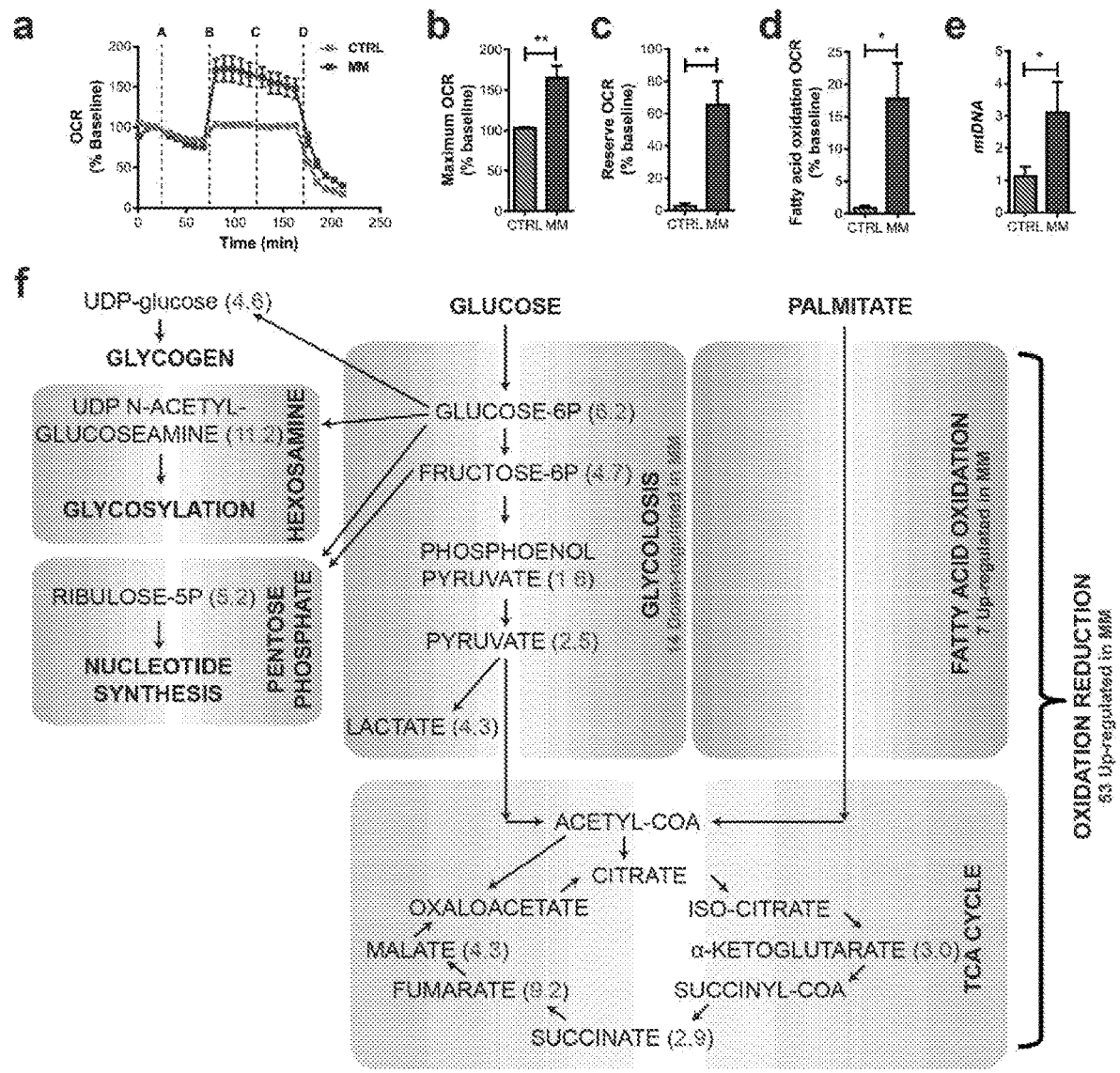

FIG. 10: Metabolism switches from glycolysis to fatty acid oxidation in hCOs cultured in MM.
a) Seahorse mitochondrial stress test. A—oligomycin, B—FCCP, C—etmoxir, D—antimycin A/rotenone. The Seahorse stress tests were run with n=6 independent recordings from n=8 pooled hCOs per recording from hCOs cultured in CTRL medium or MM for 9 days (panels b-d).
b) Maximum OCR is higher in hCOs cultured in MM.
c) Reserve metabolic capacity is higher in hCOs cultured in MM.
d) Fatty acid oxidation is higher in hCOs cultured in MM.
e) mtDNA is higher in hCOs cultured in MM (qPCR using ND1 and RNA18S5 as an endogenous genomic control). n=4 experiments.

f) Measurements of carbon metabolites (n=2, each 12-14 pooled hCO) confirm that the metabolism in hCOs cultured in MM switches from glycolysis to fatty acid oxidation. Values in red in brackets indicate fold higher in CTRL medium vs MM. Metabolomics values are normalized to the DNA intensity in hCO cultured in MM versus CTRL medium.

Data is mean±s.e.m. *P<0.05, **P<0.01, t-test (b-d) or ratio paired t-test (e).

Figure 1:
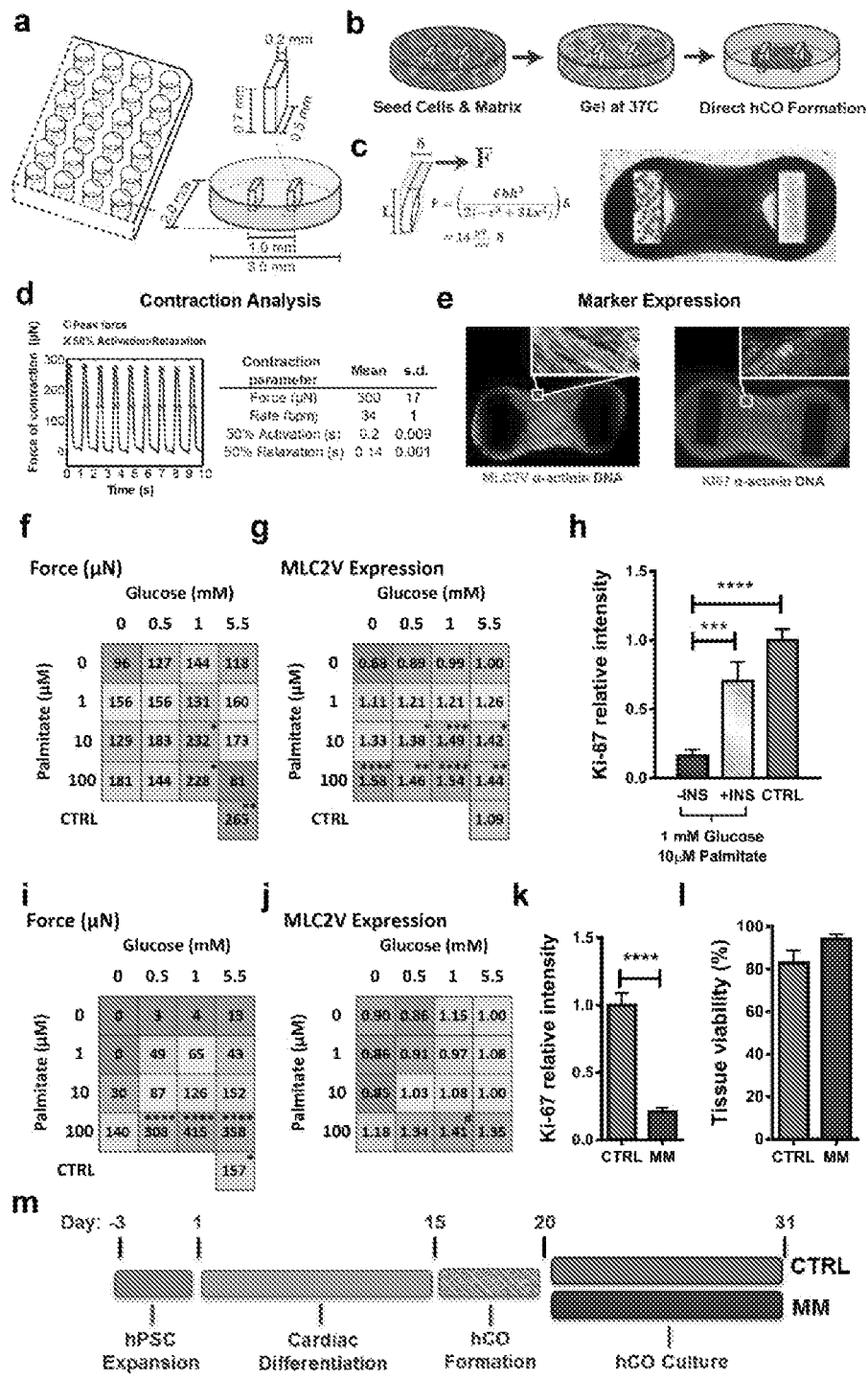
FIG. 1: The Heart-Dyno micro-tissue platform facilitates automated formation, mechanical loading and analysis of human cardiac organoids.
- a) Schematic representation of the 96-well plate Heart-Dyno. Each well has a culture insert containing an elliptical seeding well that contains two elastomeric posts.
- b) Automatic tissue formation within the Heart-Dyno. hPSC-CMs and fibroblasts are seeded within ECM and allowed to gel for 30 min at 37° C. Cells subsequently condense around the two elastomeric poles, resulting in the automated formation of a hCO.
- c) Pole-tracking can be used to approximate the force of contracion. Left: Pole deflection schematic with force approximation formulae (see SI Appendix methods). Based on the parameters of our system this results in a force equal to 14 μN per μm of post deflection. Right: Phase contrast image of a cardiac micro-tissue; crosses on the left pole indicate tracking points selected by automated contraction analysis software.
- d) Batch video analysis can be performed on each hCO to obtain contractile properties. Left: Representative force trace curve. Right: Overall contraction parameters±standard deviation from n=31 tissues cultured for 7 days in control medium. Ta: Time from 50% activation to peak. Tr: Time from peak to 50% relaxation.
- e) Whole-mount immunostaining can be used to assess hCO marker expression for screening. Representative images with confocal close-up of MLC2V, Ki-67 and α-actinin immunostaining.
- f) Screening identifies optimal glucose and palmitate concentrations for hCO force of contraction. Force heat-map in response to a full-factorial glucose (0, 0.5, 1 and 5.5 mM) and palmitate (0, 1, 10 and 100 μM) screen. Force was assessed after 5 days of serum-free culture following 2 days of hCO formation in CTRL medium. n=7-13 from 3 experiments, HES3-derived hCOs. CTRL=CTRL medium and subsequent panels (see SI Appendix methods).
- g) Palmitate induces MLC2V expression. MLC2v heat-map in response to a full-factorial glucose (0, 0.5, 1 and 5.5 mM) and palmitate (0, 1, 10 and 100 μM) screen. MLC2V expression was assessed after 5 days of serum-free culture following 2 days of hCO formation in CTRL medium. n=7-13 from 3 experiments, HES3-derived hCOs. MLC2V expression is relative to control serum-free conditions (5.5 mM glucose, no palmitate).
- h) KI67 expression is induced by insulin. Tissues were assessed after 11 days of serum-free culture following 5 days of hCO formation in CTRL medium. n=6-7 from 2 experiments, HES3-derived hCOs. Ki-67 expression is relative to CTRL.
- i) Screening identifies optimal glucose and palmitate levels in the absence of insulin. Force heat-map in response to a full-factorial glucose (0, 0.5, 1 and 5.5 mM) and palmitate (0, 1, 10 and 100 μM) screen without the presence of insulin. Force was assessed after 11 days of serum-free culture following 5 days of hCO formation in CTRL medium. n=6-15 from 3 experiments, HES3-derived hCOs.
- j) Palmitate induces MLC2V expression. MLC2v heat-map in response to a full-factorial glucose (0, 0.5, 1 and 5.5 mM) and palmitate (0, 1, 10 and 100 μM) screen in the absence of insulin. MLC2V expression was assessed after 11 days of serum-free culture following 5 days of hCO formation in CTRL medium. n=6-9 from 3 experiments, HES3-derived hCOs. MLC2V expression is relative to control serum-free conditions (5.5 mM glucose, no palmitate).
- k) KI67 expression is reduced in serum-free medium containing 1 mM glucose and 100 μM palmitate without insulin (now termed maturation medium, MM). Tissues were assessed after 11 days of serum-free culture following 5 days of hCO formation in CTRL medium, KI67 expression is relative to CTRL medium. n=6-8 from 2 experiment, HES3-derived hCOs.
- l) Culture of hCO maintains high tissue viability in CTRL medium or MM after 11 days of culture following 5 days of hCO formation in CTRL medium. n=16 experiments with 733 and 717 tissues, respectively, HES3-derived hCOs.
- m) Culture schematic of finalised cardiac maturation protocol, indicating timing and duration of hPSC expansion, cardiac differentiation, and hCO formation and culture in CTRL or MM media.

FIG. 1*l*: hPSC-CM proliferation and WNT-β-catenin signaling are repressed in hCOs cultured in MM.
   a) Culture of hCOs in MM (total 11 days) reduces hPSC-CM (α-actinin) proliferation (Ki-67). n=11-14 hCOs from 3-4 experiments. 4,396 hPSC-CMs were manually counted. Scale bars=20
   b) Culture of hCOs in MM (total 11 days) reduces hPSC-CM (α-actinin) mitosis (pH3). n=10 from 5 experiments. 7,838 hPSC-CMs were manually counted.
   c) Activated β-catenin intensity in hCOs cultured in different metabolic conditions after 48 h reveals that lack of insulin is responsible for a decrease in activated β-catenin. n=6-13 from 3 experiments.
   d) Representative immunostaining of activated β-catenin in hCO in MM with and without insulin. Scale bars=200 μm. Inset above coloured image is white coloured activated β-catenin alone.
   e) Ki-67 intensity in hCOs cultured in different metabolic conditions after 48 h reveals that lack of insulin is responsible for the initial drop in cell cycle activity. n=6-13 from 3 experiments. Scale bars=20
   f) Cell cycle activity (Ki-67) and activated β-catenin were highly correlated in hCOs cultured under different metabolic conditions. n=146 from 3 experiments.
   g) Re-introduction of insulin for 48 h after longer term culture (9 days in MM) could not restore proliferation (Ki-67) of hPSC-CMs (α-actinin), representative immunostaining.
   h) Ki-67 intensity in hCOs following re-introduction of insulin for 48 h after longer term culture (9 days in MM) could not restore proliferation. n=10-11 hCOs from 2 experiments.
   i) Quantification of proliferating (Ki-67) hPSC-CMs (α-actinin) reveals that following re-introduction of insulin for 48 h after longer term culture (9 days in MM) could not restore proliferation. n=3-4 hCOs from 2 experiments. 2,441 hPSC-CMs were manually counted.

Scale bars=20 Data is mean±s.e.m, **P<0.01, using t-test (a). P-values calculated using t-test (b,h,i), Pearson correlation (r) and p-value (f). P<0.0001, INS-statistically different from INS+ using two-way ANOVA (c,e).

Figure 12:
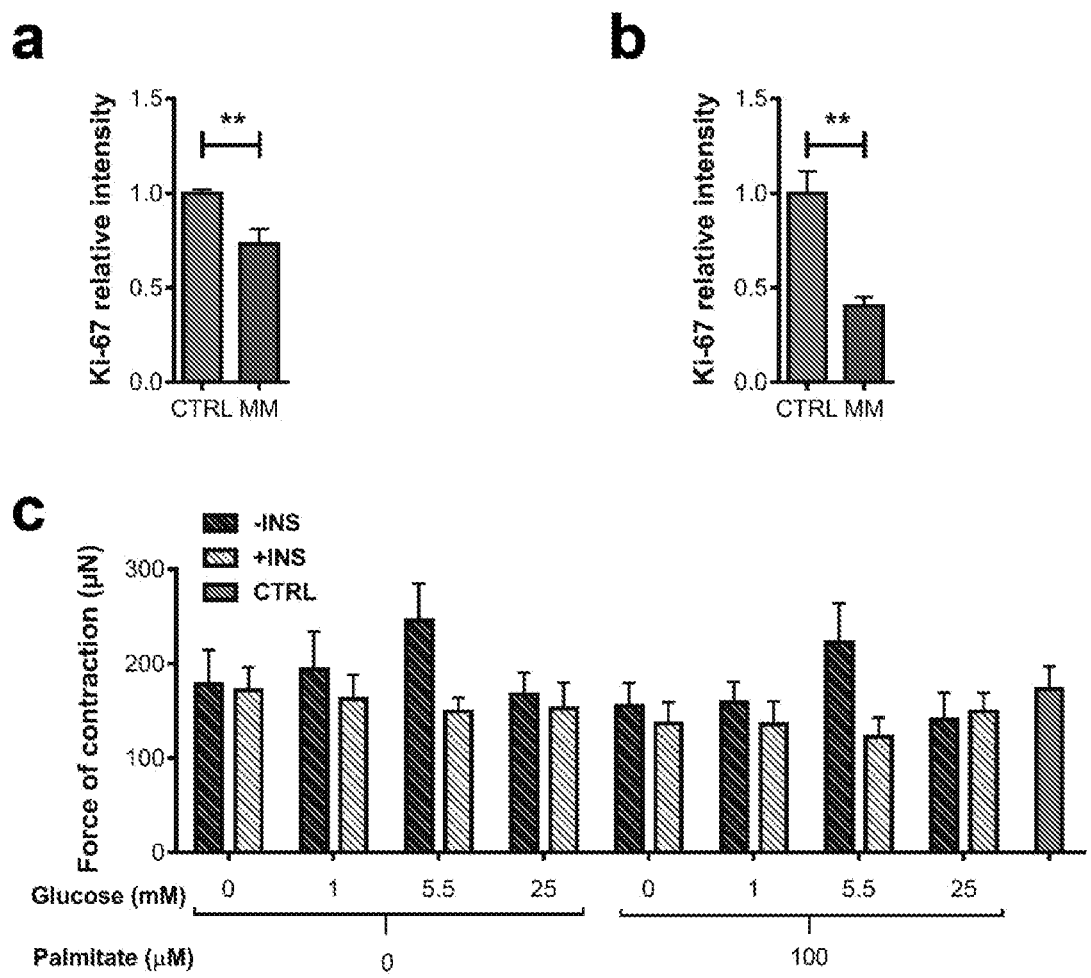

FIG. 12: Ki-67 intensity in hCO derived from different lines and force of contraction under different metabolic conditions in support of the data presented in FIG. 5.
   a) Ki-67 intensity in H9-derived hCOs. n=10.
   b) Ki-67 intensity in hIPSC-derived hCOs. n=4.
   c) Force of contraction in HES3-derived hCOs cultured in different metabolic conditions after 48 h. n=11-15 from 3 experiments.

Data is mean±s.e.m. **P<0.01, using t-test (a,b).

Figure 13:
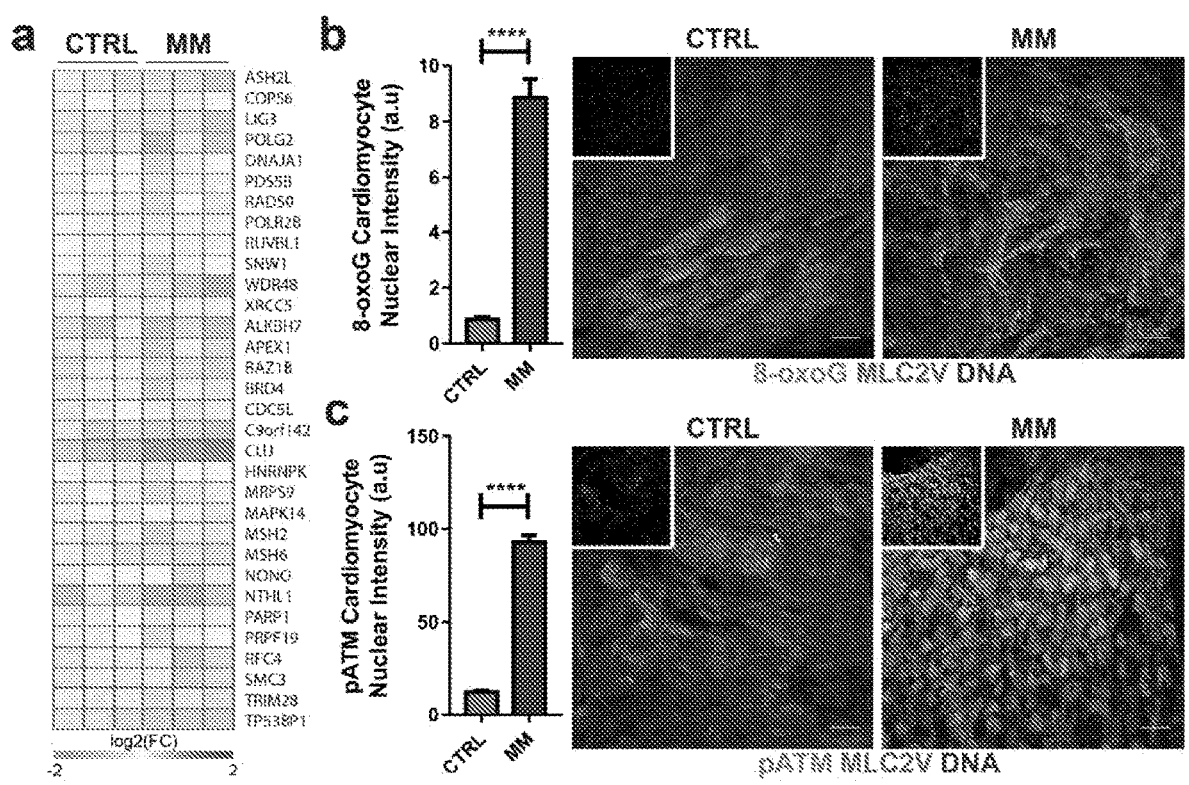

FIG. 13: hCO culture in MM induces a DDR.
   a) Heat map showing significantly regulated proteins in CTRL medium vs MM derived from proteomics data for the GO term "cellular response to DNA damage stimulus". Data presented as $log_2$ expression relative to mean for all conditions. n=3 experiments.
   b) Nuclear intensity for the oxidative base modification in DNA 8-oxo-7,8-dihydroguanine (8-OxoG) showing an increase in hPSC-CMs (MLC2v) cultured in MM. n=120-180 hPSC-CM nuclei. Inset is white coloured 8-OxoG alone.
   c) Nuclear intensity for phosphorylated (Ser1987) ATM (pATM) showing an increase in hPSC-CM (MLC2v) cultured in MM. n=120-240 hPSC-CM nuclei. Inset is white coloured pATM alone.

Scale bars=20 Data is mean±s.e.m. ****P<0.0001, using t-test (b,c)

Figure 14:
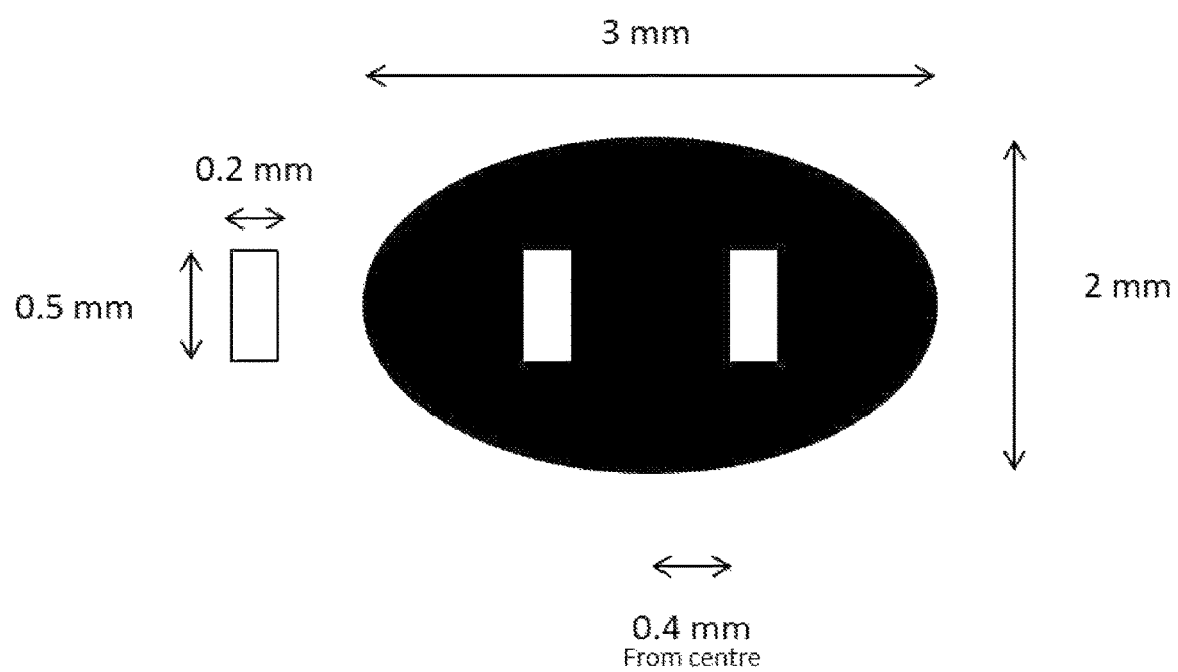

FIG. 14. Preferred embodiment of a well of a Heart-Dyno device.

Figure 15:
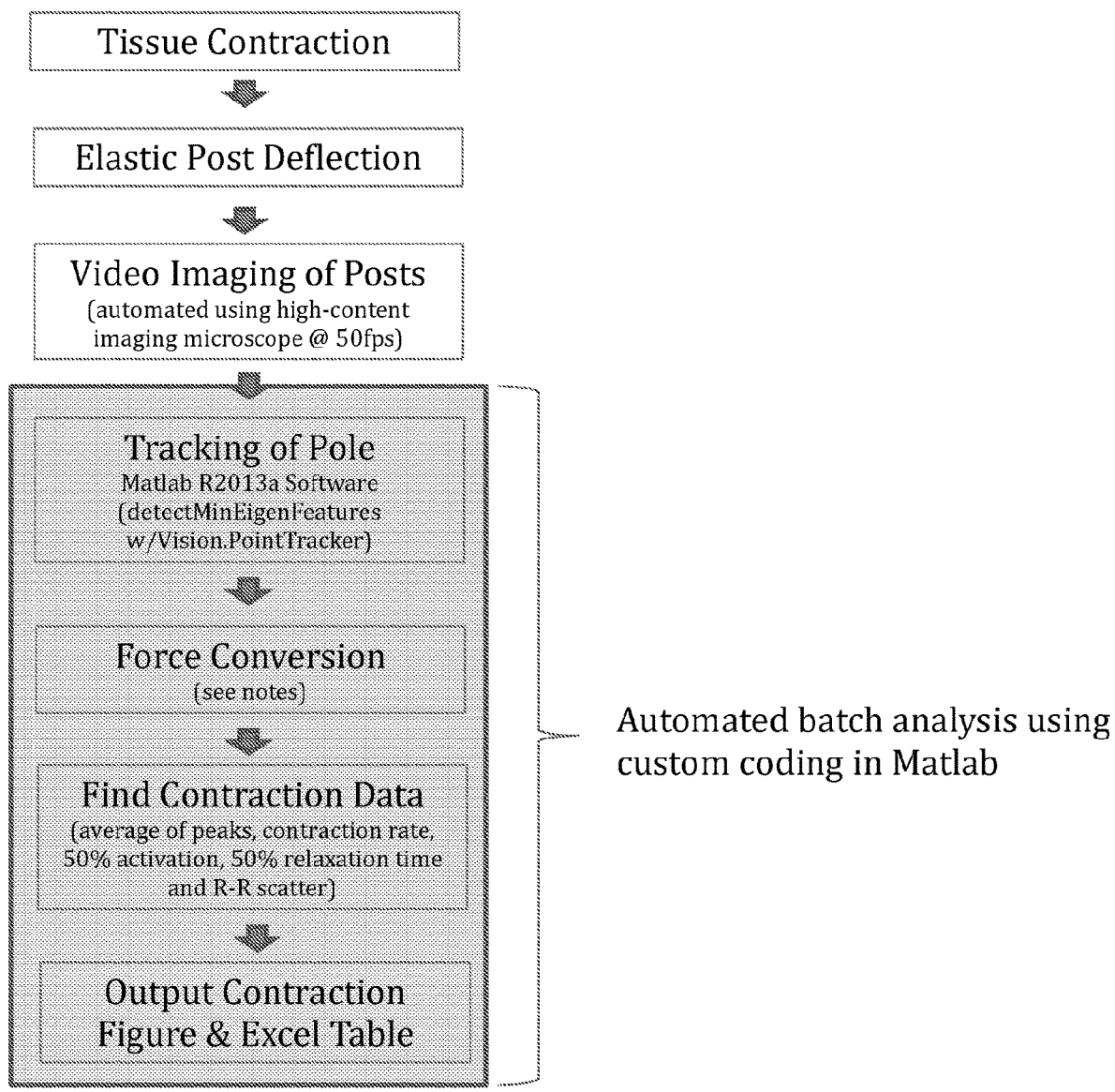

FIG. 15. Schematic depiction of system for measuring contractile force.

Figure 16:
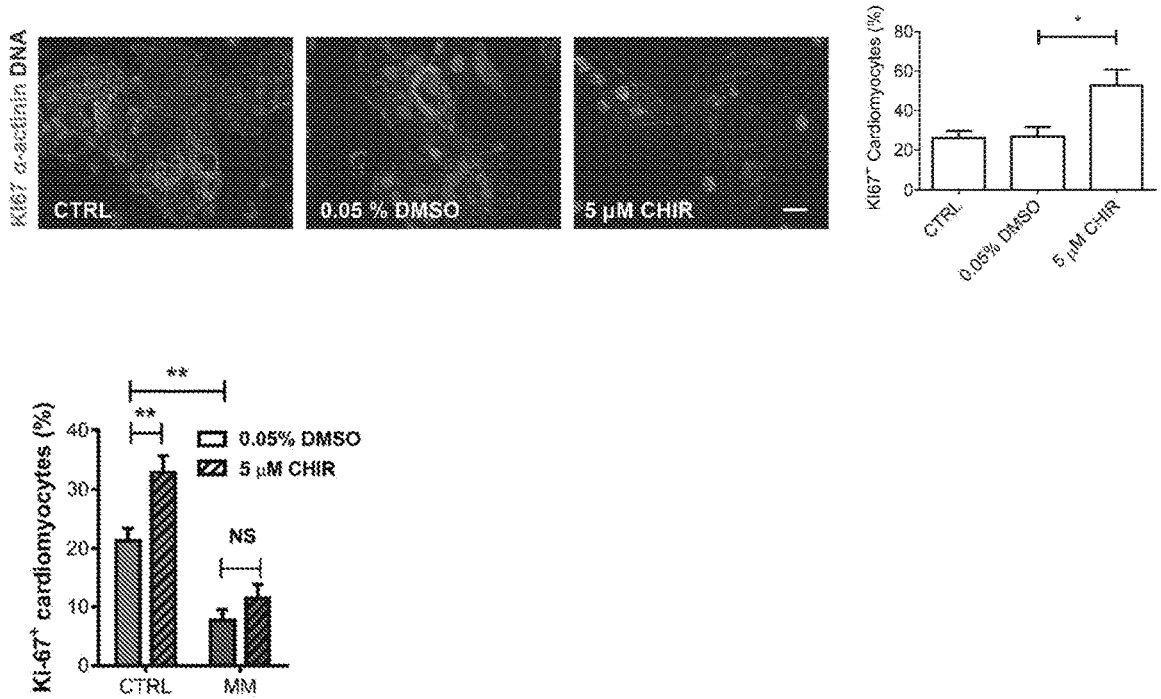

FIG. 16. Non-proliferative status of cardiac organoids matured in maturation medium.
   a) Quantification of proliferating (Ki-67) hPSC-CMs (α-actinin) cultured in 2D gelatin coated plated in CTRL medium in response to 5 μM CHIR99021 and 0.05% DMSO (control). Data is 4 independent experiments. 3160 cardiomyocytes were manually counted in these experiments.
   b) Quantification of proliferating (Ki-67) hPSC-CMs (α-actinin) confirms hCOs cultured in MM have a blunted proliferative response to CHIR99021 (24 h treatment). n=7-8 from 2 experiments. 10,609 hPSC-CMs were manually counted.

Scale bars=20 Data is mean±s.e.m. * P<0.05, P<0.01, **P<0.0001, using ANOVA with Dunnett's (a) or Tukey's post-test (b).

Figure 17:
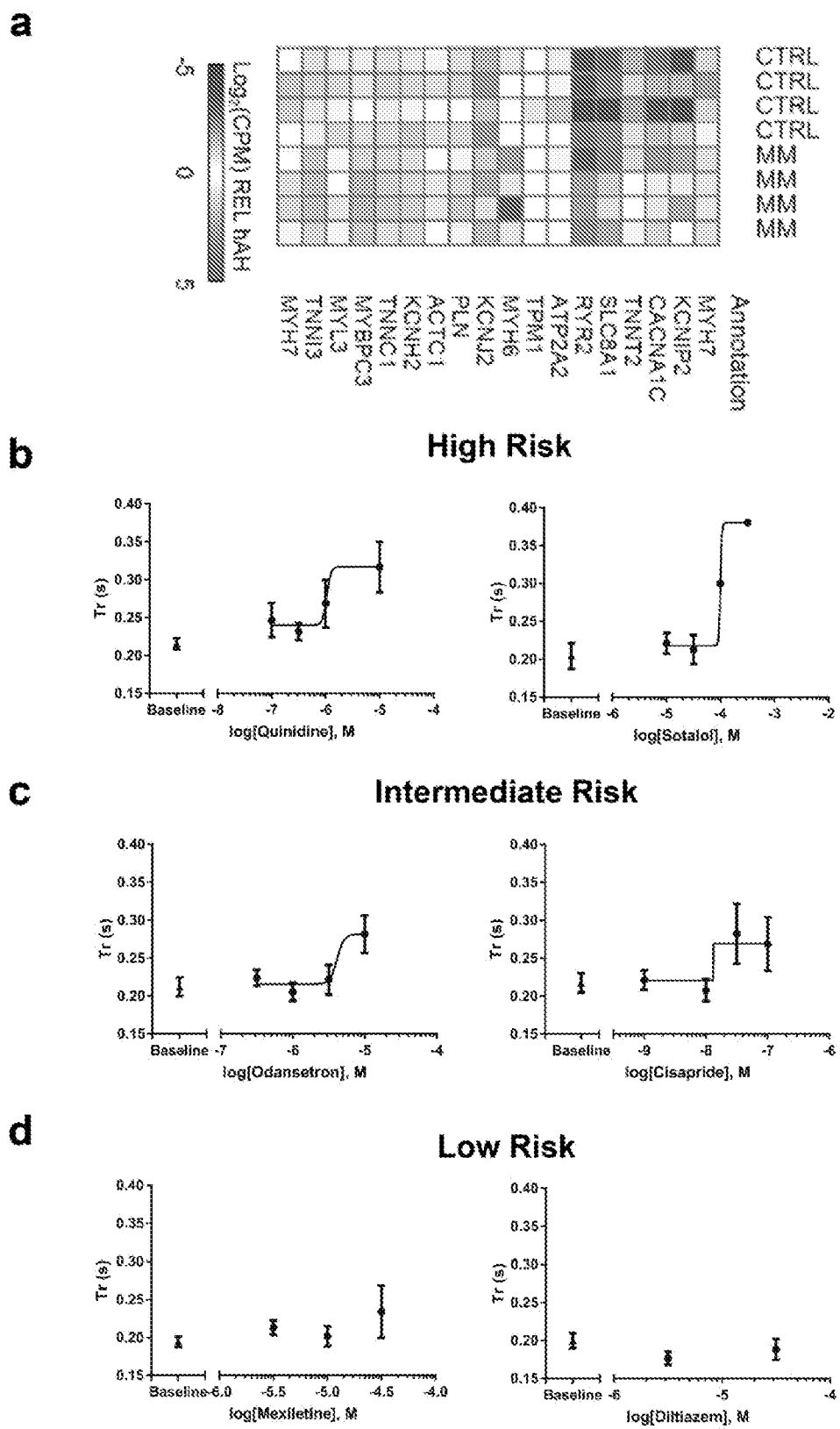

FIG. 17: Toxicology screening using mature hCO.
   a) Human cardiomyocytes express all the major ion channels, calcium handling proteins and sarcomeric proteins for contraction making them a good model for toxicology screening (data from RNA-seq FIG. 6).
   b) Concentration-response curves for 50% relaxation time (Tr) in mature hCO to known molecules with a high risk of arrhythmic effects.
   c) Concentration-response curves for 50% relaxation time (Tr) in mature hCO to known molecules with a medium risk of arrhythmic effects.
   d) Concentration-response curves for 50% relaxation time (Tr) in mature hCO to known molecules with a low risk of arrhythmic effects.

Data is presented as mean±S.E.M. n=4-6 hCO per molecule tested. hAH—human Adult Heart.

Figure 18:
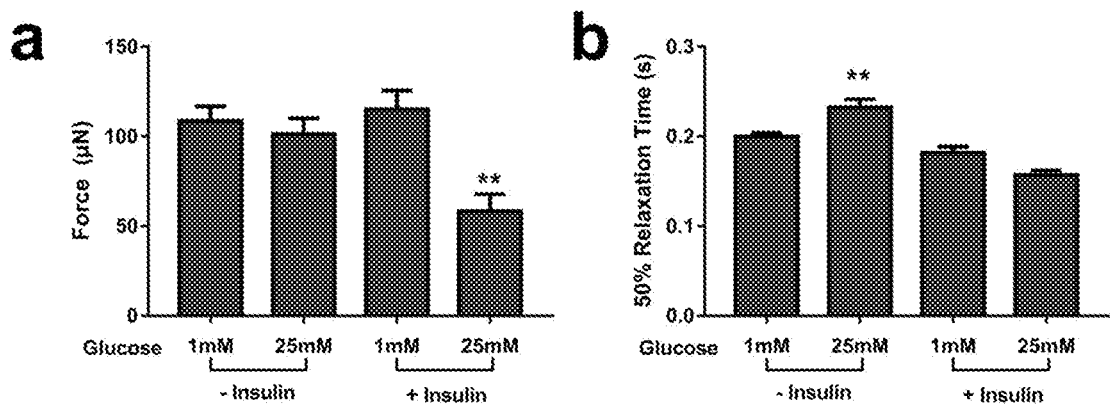

FIG. 18: Diabetic conditions promote Heart Failure with preserved Ejection Fraction (HFpEF)-like alterations in cardiac function.
   a) Force of contraction with altered glucose/insulin provision
   b) Relaxation time (diastolic function) with altered glucose/insulin provision n=8, ** p<0.01 from baseline maturation medium (1 mM glucose, no insulin) using ANOVA with Tukey's post-test.

Figure 19:
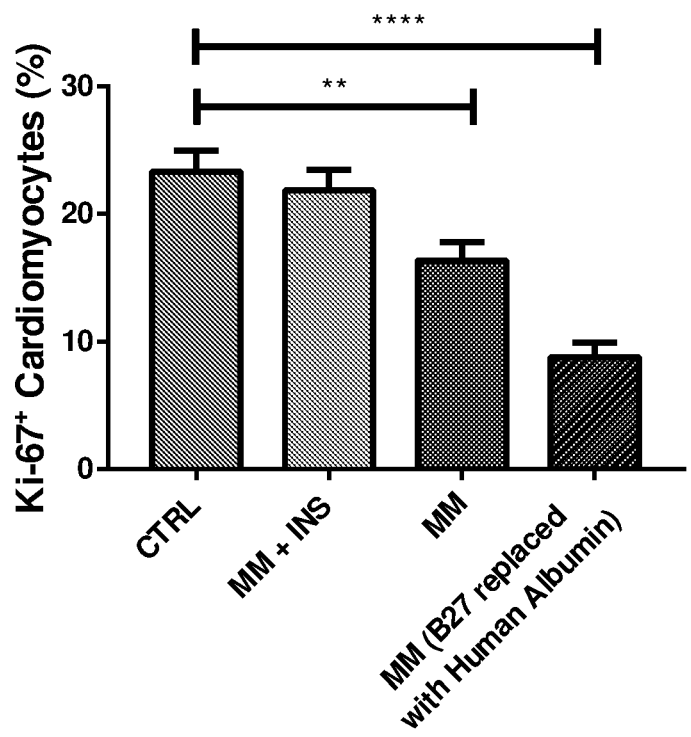

FIG. 19: Maturation medium (MM) also reduces cell cycle activity in 2D cardiomyocyte cultures.

Quantification of proliferating (Ki-67$^+$) cardiomyocytes (α-actinin$^+$) after 3 days of culture in different medium compositions. n=8-12 wells. Data is presented as mean±S.E.M.,  P<0.01, ** P<0.0001, using ANOVA with Tukey's post-test.

DETAILED DESCRIPTION

The present invention has arisen from work that aimed to screen for the effects of metabolism on cardiac maturation.

One aspect of this work was the development of a 96-well device for high-throughput screening in bioengineered human heart tissues. The heart dynamometer (or "Heart-Dyno") was designed to form dense muscle bundles by limiting tissue size and the geometry of the device enables automated tissue formation, culture and force of contraction analysis without any tissue handling. Using the Heart-Dyno, completely serum-free 3D culture conditions have been defined that promote structural, electrophysiological, metabolic and proliferative maturation of hPSC-derived cardiomyocytes and cardiac organoids. The present invention is therefore directed to a method, culture medium and/or system for facilitating structural, electrophysiological, metabolic and/or proliferative maturation of stem cell-derived cardiac tissue, such as in the form of cardiac organoids.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described.

As used herein, except where the context requires otherwise, the term "comprise" and variations of the term, such as "comprising", "comprises" and "comprised", are not intended to exclude further additives, components, integers or steps.

It will be appreciated that the indefinite articles "a" and "an" are not to be read as singular indefinite articles or as otherwise excluding more than one or more than a single subject to which the indefinite article refers. For example, "a" cell includes one cell, one or more cells and a plurality of cells.

As used herein, the term "about" qualifies a stated value to encompass a range of values above or below the states value. Preferably, in this context the range may be 2, 5 or 10% above or below the stated value. By way of example only, "about 100 µM" may be 90-110 µM, 95-105 µM or 98-102 µM.

For the purposes of this invention, by "isolated" is meant material that has been removed from its natural state or otherwise been subjected to human manipulation. Isolated material (e.g., cells) may be substantially or essentially free from components that normally accompany it in its natural state, or may be manipulated so as to be in an artificial state together with components that normally accompany it in its natural state.

By "enriched" or "purified" is meant having a higher incidence, representation or frequency in a particular state (e.g an enriched or purified state) compared to a previous state prior to enrichment or purification.

In certain aspects, the invention is broadly directed to a cell culture medium, system and/or method suitable for differentiating cardiac cells, such as cardiomyocytes, from progenitor cells such as human embryonic stem cells or induced pluripotent stem cells.

An aspect of the invention provides a cardiac cell maturation medium comprising a base medium, one or more fatty acids, glucose and albumin.

Another aspect of the invention provides a cardiac cell culture system comprising:
  the cardiac cell maturation medium of the first aspect; and
  (ii) a cardiac cell culture vessel comprising a plurality of wells that each comprise opposed poles that extend substantially perpendicularly from a basal surface of the well.

Yet another aspect of the invention provides a method of culturing cardiac cells, said method including the step of contacting one or more progenitor cells with the cardiac cell maturation medium of the first aspect for sufficient time and under suitable conditions to induce or promote maturation of one or a plurality of the one or more progenitor cells into cardiomyocytes.

A "progenitor cell" is a cell which is capable of differentiating along one or a plurality of developmental pathways, with or without self-renewal. Typically, progenitor cells are unipotent or oligopotent and are capable of at least limited self-renewal.

The terms "human embryonic stem cell", "hES cell" and "hESC" refer to cells derived, obtainable or originating from human embryos or blastocysts, which are self-renewing and pluri- or toti-potent, having the ability to yield all of the cell types present in a mature animal. Human embryonic stem cells (hESCs) can be isolated, for example, from human blastocysts obtained from human in vivo preimplantation embryos, in vitro fertilized embryos, or one-cell human embryos expanded to the blastocyst stage.

The terms "induced pluripotent stem cell" and "iPSC" refer to cells derivable, obtainable or originating from human adult somatic cells of any type reprogrammed to a pluripotent state through the expression of exogenous genes, such as transcription factors, including OCT4, SOX 1, 2, 3, 15 and 18, KLF4, LIN28, Glis 1 and c-MYC, although without limitation thereto.

The terms "differentiate", "differentiating" and "differentiated", relate to progression or maturation of a cell from an earlier or initial stage of a developmental pathway to a later or more mature stage of the developmental pathway. It will be appreciated that in this context "differentiated" does not mean or imply that the cell is fully differentiated and has lost pluropotentiality or capacity to further progress along the developmental pathway or along other developmental pathways. Differentiation may be accompanied by cell division.

As used herein "cardiomyocytes" are cardiac muscle cells also known as myocardiocytes or cardiac myocytes, that make up cardiac muscle such as found in the atria and ventricles of the heart. Each myocardial cell contains myofibrils, which are the fundamental contractile units of cardiac muscle cells. Cardiomyocytes typically contain one or two nuclei, although they may have as many as four and a relatively high mitochondrial density, facilitating production of adenosine triphosphate (ATP) for muscle contraction. Myocardial infarction causes the death of cardiomyocytes. In adults, the heart's limited capacity to regenerate these lost cardiomyocytes leads to compromised cardiac function and high morbidity and mortality.

As will be well understood in the art, the stage or state of differentiation of a cell may be characterized by the expression and/or non-expression of one of a plurality of markers. In this context, by "markers" is meant nucleic acids or proteins that are encoded by the genome of a cell, cell population, lineage, compartment or subset, whose expression or pattern of expression changes throughout development. Nucleic acid marker expression may be detected or measured by any technique known in the art including nucleic acid sequence amplification (e.g. polymerase chain reaction) and nucleic acid hybridization (e.g. microarrays, Northern hybridization, in situ hybridization), although without limitation thereto. Protein marker expression may be detected or measured by any technique known in the art including flow cytometry, immunohistochemistry, immunoblotting, protein arrays, protein profiling (e.g 2D gel electrophoresis), although without limitation thereto. Preferably, protein markers are detected by an antibody or antibody fragment (which may be polyclonal or monoclonal) that binds the protein marker. Suitably, the antibody is labeled, such as with a radioactive label, a fluorophore (e.g Alexa dyes), digoxogenin or an enzyme (e.g alkaline phosphatase, horseradish peroxidase), although without limitation thereto. Table 1 and 2 provides particular non-limiting examples of markers, antibodies and fluorophores useful for marker detection according to the invention. Markers may alternatively be "metabolites" that are the product of metabolic processes accompanying cellular changes as a result of differentiation or development.

As generally used herein, the term "serum" refers to a substantially cell-free proteinacious blood fraction obtained or obtainable from an animal (e.g fetal bovine serum) and does not include purified or recombinant synthetic serum components such as albumin. In this context "serum free", as a serum free medium, means a complete absence of serum or may refer to no more than about 1%, 0.5%, 0.2%, or 0.1% (v/v) serum.

A particular feature of the cardiac cell culture medium disclosed herein is the selection of components or constituents that optimize the maturation of cardiomyocytes and formation of Engineered Heart Tissue (EHT) and cardiac organoids.

Initial steps of the method differentiate progenitor cells, such as hESC or iPSC, into cardiac mesoderm and then into cardiomyocytes. Initially, progenitor cells are differentiated into cardiac mesoderm in a culture medium comprising a serum-free base medium such as RPMI together with a supplement such as B27 at a preferred concentration of about 2% (v/v), in the absence of insulin. The culture medium may further comprise ascorbic acid 2 phosphate, BMP-4, Activin A, FGF-2 and a GSK-3 inhibitor such as CHIR99021. Subsequently, cells are differentiated into cardiomyocytes in the presence of a Wnt inhibitor such as IWP-4 followed by addition of insulin and ascorbic acid 2 phosphate in supplemented medium (e.g RPMI+2% B27) until collagenase digestion at about 15 days.

The collagenase-digested cardiomyocytes may then be cultured in a cardiac cell maturation medium. Suitably, the cardiac maturation medium comprises a "base medium" which may be any serum-free medium such as αMEM, DMEM, Iscove's medium or RPMI1640. In some embodiments, the base medium is α-MEM GlutaMAX. Suitably, the cardiac cell maturation medium is serum-free. The cardiac cell maturation medium may further comprise a supplement such as, but not limited to, B27. In a preferred embodiment, the cardiac cell maturation medium comprises albumin, such as purified or recombinant bovine serum albumin or human serum albumin. The albumin may be present in supplements such as B27 or may be included as a separate component of the medium. Suitably, the concentration of albumin is preferably no less than about 2 mg/mL, less than 1 mg/mL, less than 0.5 mg/mL, less than 0.2 mg/mL or as low as 0.1 or 0.05 mg/mL. The cardiac cell maturation medium may further comprise L-ascorbic acid 2 phosphate.

The cardiac cell maturation medium may be suitable for producing cardiac cell suspensions, monolayers or two-dimensional "2D" cultures, such as shown in FIG. 20.

In other embodiments where a three-dimensional "3D" cardiac tissue or organoid is to be produced, before culture in the cardiac cell maturation medium referred to above, cells are cultured in a gelling medium comprising serum-free base medium and supplement such as B27 (comprising albumin but no insulin) as described above and extracellular matrix (ECM) or components thereof. As broadly used herein, "ECM" refers to a matrix or web of molecules located outside or external to cells that regulate cell-cell communication, cell signalling, cell adhesion, spacing, location and/or orientation, although without limitation thereto. The molecular components of ECM may include proteoglycans, heparan sulphate, chondroitin sulphate, keratin, collagens (e.g types I-XIV), elastins, laminin and fibronectin, although without limitation thereto.

In some embodiments, the ECM may be present in the form of Matrigel™. The concentration of Matrigel™ may be about 2-20% (v/v), preferably at about 5-15% (v/v), more preferably about 7-12% (v/v) or 8-10% (v/v) or advantageously about 9%. (v/v) of gelling medium. Suitably, collagen is also present at a concentration in excess of about 2 mg/mL, or advantageously about 2.6 mg/mL of gelling medium. This is approximately about 0.23 mg/1.5×10⁶ cells. Suitably, the cardiomyocytes are gelled in the gelling medium comprising Matrigel™ and collagen, typically at about 37° C. for about 30 minutes. The presence of Matrigel™, particularly at higher concentrations such as 9%, is advantageous for the long term structural integrity of 3D cardiac tissues produced in the Heart Dyno, which can be compromised by cellular tension causing "necking", where the cardiac tissue mass breaks away from the opposed poles of the Heart Dyno.

After gelling, the cardiomyocytes are matured in the cardiac maturation medium comprising one or more fatty acids, albumin and glucose. Similarly, cardiomyocytes cultured as a "2D" monolayer are matured in the cardiac maturation medium comprising one or more fatty acids, albumin and glucose. The one or more fatty acids and glucose may be present at a concentration ratio of about 1:5 to about 1:60, about 1:7 to 1:20. Preferably, the one or more fatty acids and glucose are present at a concentration ratio of about 1:10. The fatty acid may be any carboxylic acid with a saturated or mono- or poly-unsaturated aliphatic chain that is capable of acting as a substrate for oxidative fatty acid metabolism in a mammalian cell. Preferably the fatty acid has an aliphatic chain that comprises twelve (12) to twenty (20) carbon atoms (i.e $C_{12}$-$C_{20}$ fatty acids). Preferably, the fatty acid has an aliphatic chain that comprises sixteen (16) or eighteen (18) carbon atoms (i.e a $C_{16}$ or $C_{18}$ fatty acid). The fatty acid may be linolenic acid, palmitic acid, linoleic acid or oleic acid, although without limitation thereto. In a particular embodiment, the fatty acid is, or comprises, palmitic acid. The fatty acid such as palmitic acid may be present at a concentration in the range 1-1000 μM, 5-50004, 10-20004 or 50-15004. A preferred concentration of a fatty acid, such as palmitic acid, is about 10004.

A preferred concentration of glucose is about 0.5-5.5 mM, or advantageously about 1 mM.

It will also be understood that glucose includes D-glucose and any open chain, chiral and/or cyclic isomers of D-glucose that may act as substrates for glycolysis in a mammalian cell.

Typically, the cardiac cell maturation medium does not comprise insulin or comprises a minimal concentration of insulin. Suitably, the minimal concentration of insulin is a concentration that stimulates cardiomyocyte proliferation (such as measured by KI67 expression) and/or Wnt/β-catenin activation no greater than 5-10% more than that seen in the complete absence of insulin.

Although not wishing to be bound unnecessarily by theory, it is proposed that the heart shifts from a metabolism which is preferentially glycolytic in the early stages of development to a metabolism which is almost exclusively oxidative at maturity. Circulating levels of substrates thus play a major role in establishing the glycolytic metabolism encountered in the fetal heart since this stage of development is marked by a low level of fatty acids and a high level of lactate in the blood. Prenatal metabolism is characterized by a predominant use of carbohydrate and fatty acid oxidation contributes only about 15% of total energy production. Adult cardiomyocyte metabolism is almost exclusively oxidative (about 90% of total energy production). Data presented in the Examples suggest that the cardiac cell maturation medium switches energy metabolism from insulin- and glucose-dependent glycolytic metabolism to fatty acid metabolism, which correlates with inhibition of Wnt/β-catenin signalling and cell cycle progression. These conditions appear to favour cardiomyocyte maturation. However, a complete absence of glucose is not preferable, in which case a particular fatty acid:glucose ratio is preferred, as hereinbefore described.

Suitably, the cardiac cell maturation medium does not comprise TGF-β1 or comprises a minimal concentration or amount of TGF-β1. Suitably, the minimal concentration of TGFβ is less than about 2 ng/mL or preferably no more than about 1 ng/mL. Suitably, the minimal concentration of TGF-β1, if present, is for less than five (5) days of culture, preferably the initial five (5) days of culture. As will be described in more detail in the Examples, the prolonged presence of TGF-β1 within the maturation media caused significant cell death and compromised the contractile function of the EHTs.

Suitably, the cardiac cell maturation medium does not comprise a fibroblast growth factor (FGF) such as FGF2, or comprises a minimal concentration or amount of FGF2.

Another aspect of the invention provides a cardiac cell maturation system that comprises a cardiac cell culture vessel comprising a plurality of wells that each comprise opposed poles that extend substantially perpendicularly from a basal surface of the well. Suitably, the well and opposed poles are dimensioned, shaped and oriented to maximize the formation of cardiac organoids comprising dense muscle bundles that engage and surround the opposed poles. Displacement of the opposed poles caused by the muscle bundles facilitates contractile force measurements, as described in more detail in the Examples and with reference to FIG. 15.

Typically, the well, or at least the upper perimeter of the well, is substantially oval in shape. Suitably, the well comprises opposed poles spaced apart along a long axis of the well. Suitably, the poles are spaced symmetrically along the long axis. The poles may be substantially perpendicular to a base of the well, projecting no further than the upper perimeter of the well. Particular, non-limiting dimensions of the well include: a 3 mm long axis and a 2 mm short axis. The opposed poles may be block-shaped having a square or rectangular cross-section. In a particular form, the opposed poles may be rectangular in cross-section, the rectangle having dimensions of 0.2 mm by 0.5 mm. In a particular form, the opposed poles are symmetrically spaced about 1.0 mm from the centres of the poles along the long axis. A particular example of a well is shown in FIG. 14 and also FIG. 1. The cardiac maturation vessel may comprise a plurality of wells disclosed herein, such as in 24, 48, 96, 384 or other multi-well formats known in the art.

The cardiac maturation vessel may be, or may be a component of, a heart dynamometer (or "Heart-Dyno") device that forms dense muscle cell bundles for automated cardiac tissue formation, culture and force of contraction analysis. An advantage of the Heart-Dyno device is that it minimizes or even eliminates tissue handling during formation, culture and force of contraction analysis. As will be understood from the Examples, the "Heart-Dyno" device provided contractile force measurements that were particularly advantageous for developing the cell culture medium hereinbefore described. A detailed description of performing contractile force measurements is described hereinafter in the Examples and a schematic summary is shown in FIG. 15. Additionally, immunohistochemistry of cardiomyocytes may readily be performed, such as to assess cardiomyocyte proliferation (e.g. by Ki67 expression) and maturation (e.g. by expression of ventricular myosin light-chain 2).

A related aspect of the invention provides a method of identifying one or more molecules that modulate cardiac cell maturation, said method including contacting one or more cardiomyocytes in the cardiac cell culture system disclosed herein with one or more candidate molecules, whereby modification of the maturation of one or a plurality of the cardiomyocytes indicates that the candidate molecule is a modulator of cardiac cell maturation.

In one embodiment, the modulator at least partly enhances or promotes cardiac cell maturation. As will be appreciated from the foregoing, such modulators include glucose and fatty acids such as palmitate, particularly when present at a particular ratio. It will be appreciated that other modulators that at least partly enhance or promote cardiac cell maturation may be identified according to this method.

In another embodiment, the modulator at least partly inhibits or suppresses cardiac cell maturation. As will be appreciated from the foregoing, such modulators include insulin and relatively high concentrations of TGF-β1 for prolonged periods. It will be appreciated that other modulators that at least partly inhibit or suppress cardiac cell maturation may be identified according to this method. It will be understood that "at least partly inhibits or suppresses cardiac cell maturation" includes modulators that are toxic to cardiomyocytes and/or lead to cell death (e.g inducers of cardiomyocyte apoptosis).

In some embodiments the cardiomyocytes have been differentiated from progenitor cells. The progenitor cells may be, or comprise, human embryonic stem cells or induced pluripotent stem cells.

It will be appreciated that this aspect of the invention provides a method or system for identifying, assaying or screening candidate molecules that may modulate cardiomyocyte maturation. Candidate molecules may be present in combinatorial libraries, natural product libraries, synthetic chemical libraries, phage display libraries, lead compound libraries and any other libraries or collections of molecules suitable for screening.

A further aspect of the invention provides one or more cardiomyocytes or cardiac tissues or organoids comprising same, produced by the method disclosed herein.

As described previously, the cardiac cell maturation medium, maturation system and method may be suitable for producing cardiac cell suspensions, monolayers or "2D cultures".

In other particular embodiments, the cardiac cell maturation medium, maturation system and method may be suitable for producing cardiac muscle tissue in three dimensional (3D) structures such as EHT or cardiac "organoids". Organoids may be used for producing engineered or artificial cardiac tissue. For example, cardiac organoids may be incorporated within a scaffold, such as a decellularised human heart, polyester fleece or biodegradable polymer scaffold, to thereby produce a cardiac 3D structure. Also contemplated are "bioprinted" 3D cardiac structures.

By way of example only, an organ printing machine has been developed which uses a hydrogel scaffold to place human cells in a desired orientation to recreate human organs.

It will also be appreciated that the cardiomyocytes and/or cardiac organoids described herein may provide potential sources of purified, differentiated cardiomyocytes for cellular therapy of the heart. In a particular embodiment, iPSC lines derived, obtained or originating from a patient with a genetic cardiac defect or disease may be used for repair of genetic mutation(s) in vitro. Such cardiac cells, EHT or organoids could be used according to the method of the invention and then administered to the patient for autologous cellular therapy. In some embodiments, cardiac cells, EHT or organoids produced according to the invention may be administered directly to the heart in the form of a tissue patch, mat, plug, bolus or other implantable form.

It will also be appreciated that the cardiomyocytes and/or cardiac organoids described herein may provide potential sources of purified, differentiated cardiomyocytes for cardiac disease modelling. By way of example, the effect of genetic defects upon heart function may be investigated, such as by determining the contractile properties of cardiac organoids comprising cardiomyocytes having the genetic defect. In a further embodiment, the efficacy of drugs or other molecules in treating or correcting the genetic defect may be assessed cardiomyocytes and/or cardiac organoids described herein.

In other embodiments, cardiomyocytes and/or cardiac organoids described herein may be used in applications such as patient specific cardiac disease modelling and cardiac biology, such as modelling, investigating or predicting the effects of modulating gene expression (e.g gene "knock out", "knock-down" or over-expression).

Accordingly, a particular aspect of the invention provides a method of determining, assessing or monitoring the effect of one or more molecules upon a cardiac cell, tissue or organoid, said method including the steps of contacting the cardiac cell, organoid or engineered heart tissue produced according to the method disclosed herein with the one or more molecules and determining assessing or monitoring the effect of the one or more molecules upon the cardiac cell, organoid or engineered heart tissue.

It will be appreciated that this aspect of the invention provides a method for determining, assessing or monitoring the effect of one or more molecules upon a cardiac cell, tissue or organoid. The effect may be, or relate to, therapeutic efficacy in treating diseases or disorders of the heart, drug dosage determination, toxicity and/or safety (e.g assessing side-effects of a drug) and contractile properties of the cardiac cell, tissue or organoid, although without limitation thereto.

The one or more molecules may be known or pre-existing drugs or may be present in combinatorial libraries, natural product libraries, synthetic chemical libraries, phage display libraries, lead compound libraries and any other libraries or collections of molecules suitable for the method.

In particular embodiments of the method, cardiomyocytes and/or cardiac organoids may be useful for toxicity screening or for in vitro drug safety testing. There are several drugs and other molecules that are cardiotoxic, particularly causing cardiac arrhythmias, cardiomyopathy and/or acute coronary syndrome. These include cisapride, $Ca^{2+}$, $K^+$ and $Na^+$ channel blockers, β blockers and chemotherapeutic agents such as anthracyclines. Drugs may be screened against cardiomyocytes and/or cardiac organoids to determine general cardiotoxocity or to determine if cardiomyocytes or organoids obtained from progenitor cells of a particular individual display sensitivity, or not, to potentially cardiotoxic drugs or other molecules or compounds.

As previously described, in some embodiments the cardiac cell, tissue or organoid may be obtained from progenitor cells of an individual having one or more particular genetic defects. By way of example, the invention contemplates a "genetic background test" where a candidate drug or other molecule could be tested against cardiomyocytes and/or cardiac organoids disclosed herein having different genetic backgrounds to determine whether there are differential drug efficacies and/or side effects that correlate with a particular genetic background. This may enable selection of appropriate drug therapies for patients with a particular genetic background.

So that the invention may be readily understood and put into practical effect, reference is made to the following non-limiting Examples.

Examples

Introduction

The mammalian heart undergoes maturation during postnatal life to meet the increased functional requirements of the adult. However, the key drivers of this process remain poorly defined. We are currently unable to recapitulate postnatal maturation in human pluripotent stem cell-derived cardiomyocytes (hPSC-CM), limiting their potential as a model system to discover regenerative therapeutics. Here, we provide a summary of our studies where we developed a 96-well device for functional screening in human pluripotent stem cell-derived cardiac organoids (hCOs). Through interrogation of >10,000 organoids, we systematically optimize parameters, including extracellular matrix, metabolic substrate and growth factor conditions that enhance cardiac tissue viability, function and maturation. Under optimized maturation conditions, functional and molecular characterization revealed that a switch to fatty acid metabolism was a central driver of cardiac maturation. Under these conditions hPSC-CMs were refractory to mitogenic stimuli and we found key proliferation pathways including β-catenin and YAP1 were repressed.

Methods

Human Pluripotent Stem Cells

Ethical approval for the use of human embryonic stem cells (hESCs) was obtained from The University of Queensland's Medical Research Ethics Committee (2014000801) and was carried out in accordance with the National Health and Medical Research Council of Australia (NHMRC) regulations. HES3 (female) and H9 (female) hESCs (WiCell) or hiPSC (female, Sendai-virus reprogrammed CD34$^+$ cells ATCC-BXS0116, ATCC) were maintained as TypLE (ThermoFisher Scientific) passaged cultures using mTeSR-1 (Stem Cell Technologies)/Matrigel (Millipore). Karyotyping and DNA fingerprinting were performed as a quality control.

Human RNA Sample

The adult human heart sample was obtained from Clontech. The adult sample was pooled from 3 hearts from 30-39 year old Caucasian males who died from trauma.

Human Proteomics Sample

The human adult heart sample was obtained from a healthy 49 year old female and snap frozen under ethical approval from The University of Sydney (2012/2814) and was carried out in accordance with the National Health and Medical Research Council of Australia (NHMRC) regulations.

Neonatal Rat Ventricular Cardiomyocytes

Cardiomyocytes were derived from P1 Sprague-Dawley neonatal rats, as previously described (60). 1-2 day old neonatal rats (Sprague Dawley) were used for cardiomyocyte isolation and handled in accordance with the Australian code of practice for care and use of animals for scientific purposes under ethics approval from the University of Queensland Ethics Committee. Briefly, neonatal rats were sacrificed and hearts were excised, washed in ADS buffer and atria removed. Myocytes were isolated using collagenase II and separated with Percoll gradients. Percoll gradients were constructed by layering 1:1.2 Percoll:ADS layer on a 1:0.5 Percoll:ADS layer in a 15 ml Falcon tube. Isolated myocytes were plated in CTRL medium (see below) on gelatine coated glass cover-slips at $1 \times 10^5$ cells/cm$^2$ and allowed to recover overnight before experiments.

Heart-Dyno Fabrication

Heart-dyno culture inserts were fabricated using standard SU-8 photolithography and PDMS moulding practices (16). Micro-fabricated cantilever array designs were drafted with DraftSight (Dassault Systems) and a number of different designs were initially tested for feasibility. Photomasks of the design were then plotted with a MIVA photoplotter onto 7-inch HY2 glass plates (Konica Minolta). SU-8 photolithography on 6-inch silicon wafer substrates formed the structures to a depth of ~700 μm. Briefly, silicon wafers were cleaned with acetone, isopropanol and $N_2$, then degassed at 150° C. for 30 min. SU-8 2150 photoresist (Microchem) was spin coated and soft baked four times to build the SU-8 to the required thickness. The wafer was then exposed to UV light under the photomask for a total dose of 1082 mJ/cm$^2$. The exposed wafer was then post exposure baked (5 min at 65° C.; 40 min at 95° C.; 4 min at 65° C.), and developed in propylene glycol monomethyl ether acetate for 45 min in a sonicator bath. Final feature height was measured with an optical surface profiler (Veeco). The Heart-Dyno was moulded by soft lithography with poly(dimethylsiloxane) (PDMS; Sylgard 184, Dow Corning; mixed in 10:1 ratio of monomer:catalyst), with curing at 65° C. for 35 min. The molds were cut using a 6 mm hole punch and placed into 96-well plates, after which they were then sterilized with 70% ethanol and UV light, washed with PBS, and coated with 3% BSA (Sigma) to prevent cell attachment to the bottom of the wells.

Cardiac Differentiation

Cardiac cells were produced using recently developed protocols (13, 56, 58). hPSCs were seeded at $2 \times 10^4$ cells/cm$^2$ in Matrigel-coated flasks and cultured for 4 days using mTeSR-1. They were then differentiated into cardiac mesoderm using RPMI B27-medium (RPMI1640 GlutaMAX+ 2% B27 supplement without insulin, 200 μM L-ascorbic acid 2 phosphate sesquimagnesium salt hydrate (Sigma) and 1% Penicillin/Streptomycin (all ThermoFisher Scientific unless otherwise indicated) containing 5 ng/ml BMP-4 (RnD Systems), 9 ng/ml Activin A (RnD Systems), 5 ng/ml FGF-2 (RnD Systems) and 1 μM CHIR99021 (Stem Cell Technologies) with daily medium exchange for 3 days. Subsequently, they were specified into a hPSC-CM/stromal cell mixture using RPMI B27—containing 5 μM IWP-4 (Stem Cell Technologies) followed by another 7 days of RPMI B27+(RPMI1640 GlutaMAX+2% B27 supplement with insulin, 200 μM L-ascorbic acid 2 phosphate sesquimagnesium salt hydrate and 1% Penicillin/Streptomycin) with medium exchange every 2-3 days. The differentiated cells were then cultured in RPMI B27+ until digestion at 15 days using 0.2% collagenase type I (Sigma) in 20% fetal bovine serum (FBS) in PBS (with $Ca^{2+}$ and $Mg^{2+}$) for 60 min at 37° C., followed by 0.25% trypsin-EDTA for 10 min. The cells were filtered using a 100 μm mesh cell strainer (BD Biosciences), centrifuged at 300×g for 3 min, and resuspended at the required density in CTRL medium: α-MEM GlutaMAX, 10% FBS, 200 μM L-ascorbic acid 2 phosphate sesquimagnesium salt hydrate and 1% Penicillin/Streptomycin. Based on flow cytometry the cells generated and used for tissue engineering were ~70% α-actinin$^+$/CTNT$^+$ hPSC-CMs with the rest being predominantly CD90$^+$ stromal cells (13).

hCO Fabrication

CTRL medium: α-MEM GlutaMAX (ThermoFisher Scientific), 10% fetal bovine serum (FBS) (ThermoFisher Scientific), 200 μM L-ascorbic acid 2 phosphate sesquimagnesium salt hydrate (Sigma) and 1% Penicillin/Streptomycin (ThermoFisher Scientific). For each hCO, $5 \times 10^4$ cardiac cells in CTRL medium were mixed with collagen I to make a 3.5 μl final solution containing 2.6 mg/ml collagen I and 9% Matrigel. The bovine acid-solubilized collagen I (Devro) was first salt balanced and pH neutralized using 10×DMEM and 0.1 M NaOH, respectively, prior to mixing with Matrigel and cells. The mixture was prepared on ice and pipetted into the Heart-Dyno. The Heart-Dyno was then centrifuged at 100×g for 10 s to ensure the hCO form halfway up the posts. The mixture was then gelled at 37° C. for 30 min prior to the addition of CTRL medium to cover the tissues (150 μl/hCO). The Heart-Dyno design facilitates the self-formation of tissues around in-built PDMS exercise poles (designed to deform ~0.07 μm/μN). The medium was changed every 2-3 days (150 μl/hCO). hCOs were cultured in CTRL medium for formation and then changed to serum-free media as indicated for experiments. For all screening experiments, after hCO formation, hCOs were cultured in serum-free conditions comprising DMEM without glucose, glutamine and phenol red (ThermoFisher Scientific) supplemented with 4% B27 (with or without insulin) (ThermoFisher Scientific), 1% GlutaMAX (ThermoFisher Scientific), 200 μM L-ascorbic acid 2 phosphate sesquimagnesium salt hydrate and 1% Penicillin/Streptomycin (ThermoFisher Scientific). Additions to the medium included glucose, palmitic acid (conjugated to bovine serum albumin within B27 by incubating for 2 h at 37° C., Sigma), or TGFβ-1 (Peprotech). A timeline of the finalized hCO fabrication, culture and maturation protocol can be found in FIG. 1m.

Force Analysis of hCO in Heart-Dyno

The pole deflection was used to approximate the force of contraction. A Leica DMi8 inverted high content Imager was used to capture a 10 s time-lapse of each hCO contracting in real time at 37° C. Custom batch processing files were written in Matlab R2013a (Mathworks) to convert the stacked TIFF files to AVI, track the pole movement (using vision.PointTracker), determine the contractile parameters, produce a force-time figure, and export the batch data to an Excel (Microsoft) spreadsheet.

Custom batch processing files were written in Matlab R2013a (Mathworks) to convert the stacked TIFF files to AVI, track the pole movement (using vision.PointTracker), determine the contractile parameters, produce a force-time figure, and export the batch data to an Excel (Microsoft) spreadsheet. The follow formulae were used to determine the contractile force at each time-point.

Maximum deflection at the end of a rectangular cantilever fixed at one end with force applied at a specified distance:

$$F = \left(\frac{6EI}{-x^3 + 3Lx^2}\right)\delta \quad \text{[eq. 1]}$$

$$I_{rectangle} = \frac{bh^3}{12} \quad \text{[eq. 2]}$$

Combining ea. 1 and ea. 2:

$$F = \left(\frac{Ebh^3}{2(-x^3 + 3Lx^2)}\right)\delta \quad \text{[eq. 3]}$$

Where F=force, I=moment of intertia, E=Young's modulus, b=length of the pole, h=width of the pole (direction of bending), L=height of the pole, x=position of tissue on the poles in z-direction, and δ=pole deflection.

Based on the parameters of our system: E=1500 kPa, b=0.5 mm, h=0.2 mm, L=0.7 mm, and x=0.35 mm (hCO half-way up the poles), k=14 µN/µm.

F=kδ [eq. 4] (per pole)

We validated that these parameters using a sensitive isometric force transducer (ADInstruments) and measured k=14.2±2.4 µN/µm (n=10).

Whole-Mount Immunostaining hCOs were fixed for 60 min with 1% paraformaldehyde (Sigma) at room temperature and washed 3× with PBS, after which they were incubated with primary antibodies (Table 1) in Blocking Buffer, 5% FBS and 0.2% Triton-X-100 (Sigma) in PBS overnight at 4° C. Cells were then washed in Blocking Buffer 2× for 2 h and subsequently incubated with secondary antibodies (Table 1) and Hoescht (1:1000) overnight at 4° C. They were washed in Blocking Buffer 2× for 2 h and imaged in situ or mounted on microscope slides using Fluoromount-G (Southern Biotech).

Immunostaining Analysis

For screening hCO were imaged using a Leica DMi8 high content imaging microscope for in situ imaging. Custom batch processing files were written in Matlab R2013a (Mathworks) to remove the background, calculate the image intensity, and export the batch data to an Excel (Microsoft) spreadsheet.

For more detailed images an Olympus IX81 confocal microscope or a Nikon Diskovery Spinning Disk confocal microscope for mounted imaging. For cell cycle analysis experiments 3 random fields of view were imaged and manually quantified for proliferation. These were added together to calculate the percentage of hPSC-CM proliferation in each hCO.

Flow Cytometry

Cells were dissociated to single cells for flow cytometry. hCO were first washed twice in perfusion buffer at 37° C. (130 mM NaCl, 1 mM $MgCl_2$, 5 mM KCl, 0.5 mM $NaH_2PO_4$, 10 mM HEPES, 10 mM Taurine, 10 mM glucose, 10 µM 2,3-butanedione monoxime, pH 7.4). hCO were incubated in EDTA buffer at 37° C. for 5 min (130 mM NaCl, 5 mM KCl, 0.5 mM $NaH_2PO_4$, 10 mM HEPES, 10 mM Taurine, 10 mM glucose, 5 mM EDTA, 10 µM 2,3-butanedione monoxime, pH 7.4). hCO were washed twice in perfusion buffer and then incubated in perfusion buffer plus 1 mg/ml collagenase B (Roche) for 30 min at 37° C. on a shaker at 750 rpm. hCO were then centrifuged at 1000×g for 3 min, collagenase removed, and incubated in 0.25% trypsin-EDTA for 15 min at 37° C. on a shaker at 750 rpm. Perfusion buffer with 5% FBS was then added and the single cells pelleted by centrifuging at 1000×g for 3 min. The cells were then stained for flow cytometry using published protocols, except PBS was replaced by perfusion buffer to maintain cell viability of live cells. Flow cytometry was performed on a Becton Dickinson LSR Fortessa X-20 cytometer and analyzed using Cyflogic 1.2.1 (Cyflo Ltd).

hPSC-CM Dissociation for Single Cell Electrophysiology and Calcium Imaging hPSC-CM were dissociated for 2D hPSC-CMs using the same protocol as for hCO fabrication and seeded on gelatin-coated coverslips in CTRL medium. Cells were analysed the following day.

hPSC-CMs were dissociated from hCOs 9 days after switching to MM by washing 3 times in calcium-free Tyrode's buffer (120 mM NaCl, 1 mM $MgCl_2$, 5.4 mM KCl, 22.6 mM $NaHCO_3$, 0.42 mM $NaH_2PO_4$, 5.5 mM glucose, pH 7.4) with 10 µM 2,3-butanedione monoxime (dissociation buffer). Cells were dissociated using 1 mg/ml collagenase Bin dissociation buffer for 30-60 min at 37° C. The dissociated cells were washed in dissociation buffer and centrifuged at 100×g for 3 min. They were resuspended in dissociation buffer and the calcium concentration gradually increased to 10, 50, 250 and finally 1250 µM using CTRL medium or MM with 10 µM 2,3-butanedione monoxime. The cells were centrifuged at 100×g for 3 min, resuspended in CTRL medium or MM with 10 µM 2,3-butanedione monoxime and plated on growth factor-reduced Matrigel or laminin (Sigma)-coated coverslips. After 4 h of attachment, the medium was changed to CTRL medium or MM without 10 µM 2,3-butanedione monoxime and the cells were analyzed the following day.

Electrophysiology

Electrophysiological recordings were obtained at 37° C. using a TC-124A temperature controller (Warner Instruments) mounted onto the stage of an Olympus IX-51 inverted microscope. Data were acquired with pClamp 9 software (Axon Instruments) through a 16-bit AD/DA interface (Digidata 1322A, Axon Instruments) connected to an Axoclamp 200B amplifier (Axon Instruments). Recordings were sampled at 10 kHz, low pass Bessel-filtered at 5 kHz (−3 dB cutoff) and evaluated offline with Clampfit 10 and GraphPad Prism 6. Pipettes were prepared from standard wall borosilicate glass capillaries (BF 120-69-10, Sutter Instruments) on a P-87 horizontal puller (Sutter Instruments).

hCO single hPSC-CM action potentials (APs) were recorded from dissociated cells bathed in: 140 mM NaCl, 4 mM KCl, 2 mM $CaCl_2$, 2 mM $MgCl_2$, 5 mM HEPES, 5 mM glucose, pH=7.4. Pipette potential offset and capacitance neutralization preceded whole-cell patch-clamp measurements in the current-clamp mode. Patch pipettes had resistances of 1-3 MΩ when back filled with an internal solution (10 mM NaCl, 140 mM KCl, 2 mM EGTA, 1 mM $MgCl_2$, 0.1 mM Na-GTP, 5 mM Mg-ATP, 10 mM HEPES, pH=7.2). hPSC-CMs were 'clamped' to a membrane potential of −80 mV by continuous current injection. APs were elicited at 1 Hz by applying 4 ms rectangular current pulses at 125% threshold level. hPSC-CM were classified into ventricular-, atrial-, and nodal-like according to the following criteria: ventricular-like APs had a clear plateau (a prolonged phase of at least 50 ms duration with less than 20 mV drop in membrane potential), fast upstroke (>50V/s), a large AP amplitude (>85 mV) and a small ratio of AP duration at 90% repolarization to AP duration at 50% repolarization (APD90/APD50<2.3). Atrial-like APs exhibited no clear plateau but shared all other ventricular-like criteria. Finally, nodal-like APs lacked a plateau phase and were characterized by a slower phase of repolarization (APD90/APD50>2.3).

Membrane potentials and spontaneous electrical signals were recorded from intact hCOs bathed in CTRL medium or MM with 7 µM blebbistatin to inhibit contractions. Pipette potential offset and capacitance were neutralized before impaling the tissue. Sharp electrodes had series resistances of 30-50 MS) when backfilled with 3 M KCl. Tip potentials and liquid junction potentials amounted to a few mV and were not subjected to correction.

Calcium Imaging

Cells were loaded with 2.5 µM Fluo-4 AM (ThermoFisher Scientific) added directly to the culture medium for 30 min at 37° C. The medium was changed (CTRL or MM) and left for 30 min at 37° C. prior to recordings. For recordings, the cells were stimulated at 1 Hz (using a Panlab/Harvard Apparatus Digital Stimulator) at 37° C. on an Olympus IX81 confocal microscope using line-scanning (~1 ms per line for ~10 s). Raw data were processed, peaks identified, and parameters calculated for each calcium transient in the recording and averaged for that particular cell. This was performed using a custom-written program in Matlab R2013a (Mathworks) to improve accuracy and eliminate bias.

RNA Extraction

RNA was extracted using Trizol (ThermoFisher Scientific), treated with DNAse (Qiagen) and purified using RNeasy Minielute Cleanup Kit (Qiagen).

RNA-Seq

For hCOs and the adult human heart sample, ribosomal RNA was depleted with Ribo Zero Gold and cDNA was generated with SuperScript II Reverse Transcriptase (ThermoFisher Scientific). RNA-seq libraries were created with TruSeq Stranded Total RNA kits (Illumina) and read with HiSeq SR Cluster v4 kit (Illumina) on a HiSeq 2500 sequencer. Sample read quality was determined with FASTQC and Trimmomatic (61) was used to trim poor quality sequence (<25 phred score) and adapter sequence. Each sample was mapped to hg38 with STAR (62). Mapped reads were then counted with htseq-count on union mode and differential expression analysis performed with EdgeR (v3.2.4).

Proteomics Sample Preparation

Nine hCO from either CTRL medium or MM conditions were pooled per replicate and washed 2× in PBS. Tissues were lysed in by tip-probe sonication in 6 M guanidinium chloride, 100 mM Tris pH 8.0, 10 mM tris(2-carboxyethyl) phosphine, 40 mM 2-chloroacetamide and heated to 95° C. for 5 min. The samples were cooled to 4° C. and centrifuged at 20,000×g for 10 min. The supernatant was diluted 1:1 with water followed by protein precipitation with 4 volumes of acetone. Protein pellets were washed with 80% acetone and resuspended in 10% trifluoroethanol, 100 mM Tris pH 8.0. Protein was quantified by BCA and 50 µg digested with 1 µg LysC (Wako Chemicals) for 2 h at 37° C. followed by 1 µg trypsin (Sigma) for 16 h at 37° C. Digests were diluted with 4 volumes of 0.5% trifluoroacetic acid (TFA) and desalted with C18 microcolumns packed with POROS Oligo R2/R3 reversed-phase particles (20 µm, ThermoFisher Scientific). Peptides were eluted in 50% acetonitrile, 0.1% TFA and dried by vacuum centrifugation. Peptides were quantified by Qubit fluorescence and 1 µg aliquots were removed for direct analysis by LC-MS/MS. A second aliquot of peptides were removed from each of the hCO samples (totaling 30 µg) and pooled for fractionation. Peptides from pooled hCO and myocardial tissue were fractionated on an 320 µm×30 cm in-house packed C18 µHPLC column (3 µm BEH, Waters) using an Agilent 1200 HPLC. The gradient was 0-40% Buffer B over 60 min with 2 min fractions collected followed by concatenation into 12 fractions for analysis by LC-MS/MS (Buffer A=10 mM ammonium bicarbonate pH 7.9, Buffer B=90% acetonitrile).

LC-MS/MS and Data Analysis

Peptides were analysed on a Dionex 3500RS coupled to a Q-Exactive Plus with Tune v2.4.1824 in positive polarity mode. Peptides were separated using an in-house packed 75 µm×50 cm pulled column (1.9 µm particle size, C18AQ; Dr Maisch) with a gradient of 2-30% acetonitrile containing 0.1% FA over 120 min at 250 nl/min at 55° C. An MS1 scan was acquired from 300-1500 m/z (70,000 resolution, 3e6 AGC, 100 ms injection time) followed by MS/MS data-dependent acquisition of the 20 most intense ions with HCD (17,500 resolution, 1e5 AGC, 60 ms injection time, 27 NCE, 1.2 m/z isolation width). Raw data was searched with *Andromeda*(63) in MaxQuant v1.5.3.30 (64) against the human UniProt database (January 2016) using all default settings with peptide spectral matches and protein false discovery rate (FDR) set to 1%. Label-free quantification (65) was enabled including the "match between runs" option where single-shot replicates of the hCO were matched into the pooled fractionated sample. Statistical analysis was performed in Perseus (66) and included a two-sample t-test corrected for multiple testing using Benjamini-Hochberg FDR. Only proteins quantified in all biological replicates were included in the final analysis and significance was calculated based on q<0.05.

Bioinformatics

Principal component analysis (PCA) was performed using Matlab R2013a (Mathworks) using normalised log 2 transformed count per million data outputted from EdgeR(v3.2.4) (67). The PCA included RNA-seq of hPSC-CMs cultured for 1 year or 20 days and adult and foetal human heart tissue (25). These 100 base pair, paired-end read data were obtained from the Gene Expression Omnibus (GSE62913) and analysed as above except Trimmomatic (61) and STAR (62) were run using paired-end sequencing settings. Gene ontological analysis was performed with DAVID (68) and heat-maps and hierarchical clustering was performed using GENE-E (Broad Institute).

qPCR cDNA was reverse transcribed using Superscript III (random primers) and qPCR performed using SYBR Mastermix (ThermoFisher Scientific) on a Applied Biosystems Step One Plus. The $2^{-\Delta\Delta ct}$ method was used to determine gene expression changes using 18S as the endogenous control. Primer sequences are listed in Table 2 and were used at 200 nM.

Transmission Electron Microscopy

Samples were processed for electron microscopy as described previously (69). Sections were analyzed unstained in a Jeol1011 transmission electron microscope.

Metabolite Extraction

To extract cellular metabolites, hCOs were pooled into n=12 or 14 for hCOs cultured in CTRL medium or MM (for 9 days), respectively. They were washed 3 times in 3 ml of ice cold 0.9% NaCl and the metabolites extracted using 1 ml ice cold 50% aqueous acetonitrile with multiple rounds of vortexing over a 10 min period (70). The samples were snap frozen at −80° C. until processing and analysis. The extraction solution contained 50 nM azidothymidine per sample as an internal standard to monitor extraction efficiency for HPLC-MS/MS analysis.

Central Carbon Metabolite Analysis

Intermediates of central carbon metabolism (CCM) were analysed following the method described in (71) with the following modifications—sample extracts were analysed at two concentrations to enhance the likelihood of detection for low abundance metabolites as well as to dilute highly abundant metabolites into range. Thus, 200 µl of sample extract were dried down in a vacuum centrifuge (Eppendorf Concentrator Plus, Eppendorf) for ~60 min with no heating (i.e. at room temperature) using the V-AQ program. The samples were resuspended in 50 µl of 95:5 water:acetonitrile to provide a four-fold concentrated sample, 5 µl of which was removed to a fresh vial and diluted with 95 µl of 95:5 water:acetonitrile to provide an effective five-fold dilution of the original extract. Samples were transferred to HPLC vials for CCM analysis by injection onto the HPLC-MS/MS system as described previously (71).

Seahorse Metabolic Profiling

Cellular bioenergetics (including oxygen consumption rate [OCR] and extracellular acidification rates [ECAR]) were determined on a Seahorse XF24 Extracellular Flux Bioanalyser (Seahorse Bioscience). Briefly, hCOs were washed in unbuffered assay medium (pH=7.4, Seahorse Bioscience) supplemented with glucose (5.5 mM, Sigma), sodium pyruvate (1.0 mM, ThermoFisher Scientific) and GlutaMAX (2.0 mM, ThermoFisher Scientific). Following two washes, 6-8 hCOs were seeded (in assay medium) into a 24 well XF24 cell culture microplate (Seahorse Bioscience). Eight wells, which contained unbuffered assay medium alone, were used as background controls. Specific aspects of mitochondrial and glycolytic bioenergetics were analysed during a mitochondrial stress test using consecutive administration of oligomycin (2 µM), FCCP (1.5 µM), etomoxir (4 µM) and rotenone/antimycin A (2 µM), as described previously (72).

Mitogen Screening

For neonatal rat cardiomyocytes, small molecules/growth factors were added to CTRL medium and given to the cells for 24 or 48 h: DMSO (Sigma), CHIR99021 and NRG-1 (RnD Systems). For transfection experiments, the cells were transfected for 8 h using Lipofectamine RNAiMax (3 µl/24 well) in 500 µl/24 well OptiMEM followed by a medium change into CTRL medium. The cells were transfected at 50 nM with scramble miR control (All Stars Negative Control, Qiagen), miR mimic hsa-miR-199a-3p (Qiagen) or miR mimic hsa-miR-590-3p (Qiagen). For overexpression of constitutively active Yap 1, cells were infected in CTRL medium with an adenovirus containing a mutated version of murine Yap 1, CMV-YAP(S112A) at an MOI of 10.

hCO were cultured for 6 days after seeding in the Heart-Dyno in CTRL medium prior to treatment. Small molecules were added and given to the cells for 48 h: DMSO, CHIR99021 and NRG-1. For transfection experiments, the cells were transfected for 4 h using Lipofectamine RNAiMax (3 µl/hCO) in 150 µl/hCO OptiMEM followed by a medium change into CTRL medium. The cells were transfected at 50 nM with scramble miR control, miR mimic hsa-miR-199a-3p or miR mimic hsa-miR-590-3p. For overexpression of constitutively active YAP1, hCOs were infected in with an AAV6 containing a mutated version of human YAP1, CMV-YAP(S127A) (Vector Biolabs) at 1.25-2.5×10$^{10}$ vg/hCO. For overexpression of constitutively active β-catenin hCO were infected with an AAV6 containing a mutated version of human CTNNB 1 without the amino acids 2-90, AAV6-ΔN90βCAT (Vector Biolabs), at 1.25-2.5×10$^{10}$ vg/hCO. Control AAV6-MCS or AAV6-GFP (Vector Biolabs) controls were used at the same titres in these experiments.

Quantification and Statistical Analysis

All key hCO experiments were performed with multiple hCO per condition in multiple experiments to ensure reproducibility. For screening or experiments where multiple groups were analyzed, all groups were present in each experiment including controls to ensure that results were not an artefact of comparing conditions over different experiments.

Data is presented as mean±S.E.M. unless otherwise noted. Statistics were analysed using Microsoft Excel (Microsoft) or GraphPAD Prism 6 (Graphpad Software Inc). Sample numbers, experimental repeats, statistical analyses and p-values are reported in each figure legend.

Data-Set Availability

RNA-seq data has been deposited in GEO as GSE93841 and CTRL medium versus MM hCO proteomics data has been deposited in PRIDE under PXD005736

Results

Heart-Dyno: A Miniaturized 96-Well Human Cardiac Organoid Screening Platform

To facilitate the automated formation and analysis of cardiac organoids comprising dense muscle bundles, we used SU-8 photolithography and polydimethylsiloxane (PDMS) casting to fabricate a 96-well plate containing culture inserts (FIG. 1a). We designed the elliptical geometry such that a 3.5 µl volume containing 50,000 cardiac cells would automatically condense around two elastic posts over 2 days, forming hCOs 1 mm in length (FIG. 1b, FIG. 2a). hPSC derived—cardiac cells are comprised of ~70% α-actinin$^+$/CTNT$^+$ hPSC-CMs with the rest being predominantly CD90$^+$ stromal cells (13). This ratio of hPSC-CMs to stromal cells is essential and optimal to form a functional hCO (13, 14). The elastic posts provide mechanical resistance to the contraction of the hCOs, which is required to enhance function (15). This design also allows contractile force to be approximated by tracking the movement of the poles (FIG. 1c), which we validated using force transducers. In addition, a custom-designed high-content imaging system was developed to capture 10 s videos of each hCO from each well at high speed (50 frames per second). Video files were subsequently batch analysed using a custom-written Matlab program to produce force traces and contraction data for each hCO (FIG. 1d). We further validated our 3D tissue culture and contraction analysis pipeline by assessing hCO responses to stimuli that alter the force of contraction (FIG. 2b), and which prolong relaxation time (FIG. 2c). Importantly, the Heart-Dyno was able to predict physiological responses to known pharmacological agents, including compounds with hERG toxicity that entered the clinic and were subsequently withdrawn due to arrhythmogenic side effects (cisapride) (FIG. 2c).

In addition to semi-automated analyses of force of contraction, we also developed a protocol for post-analysis of hCOs for the expression of different markers using whole-mount immunostaining combined with high-content image analysis (FIG. 1e). We validated this approach using α-actinin and Ki-67 staining to detect the pro-proliferative effects of GSK3 inhibition using CHIR99021 (16) (FIG. 2d). These initial studies validated the Heart-Dyno as a high-throughput, high-content screening platform that facilitates chronic stimulation, as well as analysis of contractile properties and marker expression.

Screening for Optimal Metabolic Substrates for hCO Maturation

We next determined whether switching metabolism from glycolysis to fatty acid oxidation could induce hCO maturation. We screened a full factorial interplay between glucose and palmitate on cardiac maturation in serum-free medium. We chose to use palmitate as a fatty acid substrate as it is one of the most abundant fatty acids circulating during the neonatal period, representing 36% of all long chain free fatty acids (17). Cardiac maturation was assessed via three primary read-outs: cardiac function (assessed by force of contraction), hPSC-CM proliferation as a marker of immaturity (assessed by Ki-67 expression) and expression of ventricular myosin light-chain 2 (MLC2v) as a maturation marker (18).

The hCO force of contraction showed a trend to increase with the addition of 10 μM and 100 μM palmitate under serum-free conditions (pooling all glucose concentrations for each palmitate concentration, p=0.007 and p=0.07 compared to 0 μM palmitate, respectively). The highest forces were produced within medium containing 1 mM glucose and 10 μM or 100 μM palmitate (FIG. 10. Concurrently, MLC2v expression also increased with the addition of palmitate (FIG. 1g). All hCOs cultured in 100 μM palmitate, in addition to hCOs cultured in 1 mM glucose with 10 μM palmitate, had increased MLC2v expression relative to serum-free controls (5.5 mM glucose without palmitate). To assess if these serum-free conditions had any detrimental effects on cell viability, we performed ELISAs for lactate dehydrogenase and cardiac troponin I and found that their levels were unaffected by the addition of palmitate, indicating that our serum-free culture conditions in hCOs did not overtly cause cell death (FIG. 2e,f). Initial glucose-palmitate screening was performed in the presence of insulin, which is commonly used in most serum-free medium supplements to improve survival and function. However, as insulin induces glycolysis and could potentially promote proliferation through its actions on PI3K/GSK3 signalling (19), it could also be preventing cardiomyocyte maturation. We found that insulin was inducing hPSC-CM proliferation under serum-free conditions (1 mM glucose and 10 μM palmitate) (FIG. 1h). Although the removal of insulin reduced cell cycle activity, this condition could potentially have effects on cellular metabolism under serum-free conditions with 1 mM glucose and 10 μM palmitate. Therefore, we next screened the full-factorial interplay between glucose and palmitate in the absence of insulin. We again saw an increase in force in the presence of palmitate, with significantly higher forces produced within tissues cultured in 100 μM palmitate even in the presence of various concentrations of glucose (0.5, 1 and 5.5 mM glucose; FIG. 1i). Palmitate once again promoted a trend to increased MLC2v expression (FIG. 1j). Culture of hCOs in serum-free medium (1 mM glucose with 100 μM palmitate and no insulin) also reduced cell cycle activity 4-fold relative to the results obtained in CTRL medium (FIG. 1k). These conditions allowed robust generation and culture of hCOs, derived from multiple hPSC lines, with viable, intact and functional tissues produced greater than 90% of the time (FIG. 1l). We subsequently termed this medium 'maturation medium' (MM) and performed extensive phenotypic analyses of hCOs using this maturation protocol (FIG. 1m).

MM does not Alter Cellular Composition in hCO

Consistent with the drop in Ki-67, we found that hCOs cultured in MM had a reduced number of cells compared with CTRL medium based on DNA intensity analysis (FIG. 3a). After dissociating hCOs, we determined that there are a similar percentage of hPSC-CMs (α-actinin) present under both CTRL medium and MM conditions (FIG. 3b,c). We also found a small but significant decrease in CD90$^+$ cells cultured in MM (13% CTRL to 10% MM, p<0.05) (FIG. 3d). Additionally, we used whole mount immunostaining to examine multiple cardiac cell populations within the hCOs and found that hPSC-CMs (α-actinin or MLC2v), stromal cells (CD90), endothelial cells assembled into tubes (CD31), and epicardial cells (WT-1) were all present in tissues cultured in CTRL medium or MM (FIG. 3e,f). In contrast to larger tissue formats such as our recent publication (13), this suggests endothelial structures are better supported in our dense miniaturized hCO format.

MM does not Further Enhance hPSC-CM Function in hCO

We analysed the contractile properties of hCOs cultured in both CTRL medium and MM in detail. We found that hCOs cultured in MM had similar forces of contraction, but reduced activation time (Ta) and reduced relaxation time (Tr) relative to hCO cultured in CTRL medium (FIG. 4a); reflecting the changes which occur during functional maturation during human cardiomyocyte development (20). To confirm these findings, we also profiled the contraction kinetics of hCOs derived from two additional cell lines, the hESC line H9 and a commercially available human induced pluripotent stem cell (hiPSC) line. Both HES3-derived and hiPSC-derived hCOs displayed increased rates of contraction and reduced Ta in MM versus CTRL medium. However, H9-derived hCO did not have increased rates of contraction or Ta in MM versus CTRL medium (FIG. 5a). This indicates that changes in Ta are rate dependent. In contrast, all lines tested had a reduced Tr in MM compared to those cultured in CTRL medium regardless of rate (FIG. 4a, FIG. 5a). This may be due to the reduction in endogenous ECM synthesis (FIG. 6f,g), as ECM production also correlates with increased relaxation time in patients with heart disease (21).

We also assessed the chronotropic and inotropic responses to isoprenaline in hCOs cultured in both CTRL medium and MM. Isoprenaline increased the rate of contraction in both media (FIG. 4b). However, isoprenaline only induced an increase in the force of contraction in hCOs cultured in MM (FIG. 4c), which is indicative of a great contractile reserve under the culture conditions tested. We found that hCOs cultured in MM had a higher calcium $EC_{50}$ for force of contraction (1.0 mM $Ca^{2+}$) than those cultured in CTRL medium (0.3 mM $Ca^{2+}$) (FIG. 4d). A low calcium $EC_{50}$ may result in a blunted isoprenaline-induced inotropic response under our hCO culture conditions containing 1.8 mM $Ca^{2+}$, as the isoprenaline response depends on the contractile reserve (22). To investigate this, we assessed the effects of isoprenaline under highly controlled paced conditions (1 Hz) at the calcium $EC_{50}$ for CTRL medium (0.3 mM) and MM (1.0 mM) hCO. Under these conditions both CTRL medium and MM had a similar increase in force of contraction and decreased 50% contraction time (FIG. 4e). The increased calcium $EC_{50}$ in hCOs cultured in MM is indicative of maturation towards adult cardiac muscle ($EC_{50}$=2.6-6.0 mM in adult (23)).

Calcium kinetics during contraction were also assessed using Fluo-4 AM calcium imaging on single cells dissociated from hCOs at 1 Hz pacing (37° C.). Single cell calcium recordings were obtained from SP hPSC-CMs as a reference, and hPSC-CMs dissociated from hCOs in CTRL medium and MM (FIG. 5b). These experiments revealed that there was increased peak amplitude, rising slope and decay in hCO relative to the SP; indicative of a more mature calcium handling system, but no differences were observed between hCOs cultured in the different media (FIG. 4f). The lack of difference in calcium handling kinetics between CTRL and MM hCOs (FIG. 4f), also supports the notion that the reduced contractile Tr in hCOs cultured in MM is due to reduced ECM production rather than changes in hPSC-CM calcium handling properties.

We next determined the electrophysiological properties of hPSC-CMs using whole-cell patch-clamp recordings from single cells dissociated from hCOs cultured in CTRL medium or MM and SP hPSC-CMs as a reference. We found that the action potential profile in hPSC-CMs from hCOs in both CTRL medium and MM resemble that of adult ventricular cardiomyocytes (FIG. 4g, ventricular hPSC-CMs quantified in FIG. 5c). However, we found no differences between hPSC-CMs derived from CTRL medium or MM hCO (FIG. 4g). As the resting membrane potentials of the hPSC-CMs dissociated from hCOs were relatively depolarized (FIG. 4g), we also recorded electrophysiological parameters in situ in the hCOs using impaling electrodes (FIG. 5d). Using this approach, we found that the hPSC-CMs in situ had resting membrane potentials of approximately −60 mV (FIG. 5d). The depolarized membrane potentials in the initial patch-clamp experiments performed on enzymatically dissociated hPSC-CMs (FIG. 4g) were likely caused by the dissociation process. Importantly, the action potential recordings using impaling electrodes in situ also confirmed that hPSC-CMs in the hCOs in both CTRL medium and MM had adult-like ventricular action potentials (FIG. 5d). Together, these results suggest that the tissue-engineered culture environment is supportive of the development of in vivo-like functional maturation, as has been previously reported (10, 14).

MM does not Further Enhance Structural Organization Supported by hCO Culture

In order to determine whether there were other sarcomere-related changes in MM, we profiled the structural organization of the hPSC-CMs in the hCOs. Transmission electron microscopy (TEM) was used to confirm the presence of clear Z-bands and I-bands in the hCO in both CTRL and MM (FIG. 7a). This was confirmed using MLC2V and α-actinin staining revealing a highly organized expression pattern, with α-actinin localized to Z-bands and MLC2V localized to I- and A-bands in hCOs cultured in either CTRL medium or MM (FIG. 7b). Titin and α-actinin staining also revealed clear delineation of α-actinin expression in the Z-bands and titin expression in the I- and A-bands (FIG. 7c). The sarcomere length was ~2.3 μm in both media (FIG. 7d), which is consistent with adult rather than immature cardiomyocytes (24). We also observed well-developed mitochondria (FIG. 7e) and t-tubules (FIG. 7f) adjacent to the sarcomeres using TEM. We confirmed the presence of t-tubules using caveolin-3 immunostaining (FIG. 7g).

Using TEM we found that there were also highly organized intercalated discs (FIG. 7h) and we confirmed the formation of cell-cell junctions using pan-cadherin (FIG. 7i) and connexin 43 staining (FIG. 7j). Together, these results further suggest that the tissue-engineered culture environment is supportive of the development of in vivo-like structure, as has been previously reported (10, 14).

MM Induces Enhanced Maturation of Cardiac Developmental Factors, Metabolism and Cell Cycle To get a broader view of the effects of MM on hCOs, we next performed RNA-seq on hCOs cultured in CTRL medium or MM, and a commercially available adult heart sample (3 pooled male hearts, 30-39 yrs). Very few contaminating cell types from other lineages were present in the hCOs, with most markers for potentially contaminating lineages expressed at similar levels in hCOs and human adult heart tissue (FIG. 8a). When we examined markers of the most prominent cell types in the heart, we found that our protocol generated hPSC-CMs, epicardial cells and fibroblastic cells, with a similar abundance of transcripts for these lineages present in hCO and human adult heart tissue (FIG. 8b). Endothelial transcripts were also present, but at lower abundance and leukocyte transcripts were low or absent in the hCOs relative to human adult heart tissue (FIG. 8b). These results are consistent with our flow cytometry and immunostaining (FIG. 3).

Principle component analysis (PCA) was performed to determine differences between our samples. For these analyses, we also included additional publically available reference data (GSE62913) including: day 20 and 1 year old hPSC-CMs, human fetal ventricles, and human adult hearts (25). When we used all transcripts (>10 counts per million), we found that hCOs clustered distinctly from other samples indicating good reproducibility between experiments (FIG. 8c). However, no two conditions clustered together, which was most likely due to the influence of different cell populations being present in each different sample (ie. hPSC-CM samples from Kuppusamy et al., (25) are pure, while our hCO samples and the heart tissues contain multiple cell types). Indeed, hCOs have fewer endothelial cells and lack leukocytes (FIG. 8b), which are abundant in native heart tissue (26). In support of this notion, the top 25 Gene Ontology (GO)-terms for the top 1000 genes that were more highly expressed in human adult heart tissue relative to hCOs cultured in MM were mostly related to immune processes (FIG. 8d). Nevertheless, we used a similar approach as Delaughter et al., (27) to profile the developmental stage of our hCO by performing PCA on transcripts expressed in cardiomyocytes (Table S6 in (27), 795 transcripts>10 counts per million). We found that the hCO from both CTRL medium and MM conditions, 1 yr old hPSC-CMs and human fetal ventricles clustered on PC1 using this approach, and were more mature than 20 day old hPSC-CMs (FIG. 6a), consistent with the maturation profiling presented in Delaughter et al., (27). Despite these differences, which are accentuated by PCA, we found that hCOs cultured in MM highly correlated to adult human heart tissue based on RNA-seq data (FIG. 6b). We also performed proteomics on hCOs cultured in CTRL medium or MM and adult human heart tissue and found that hCOs cultured in MM also closely resembled human adult heart tissue based on proteomic data (FIG. 6c).

We identified 3856 transcripts and 855 proteins that were differentially regulated between hCOs in CTRL medium or MM (FDR<0.05 and q-value<0.05, respectively, FIG. 8e,f). Using the differentially expressed genes (FIG. 6d) or proteins (FIG. 6e), we performed GO-term analysis independently on the RNA-seq (FIG. 6f) and proteomic data sets (FIG. 6g). In both cases, a reduction in glycolysis, extracellular matrix organization and actin cytoskeleton organization were identified in hCO cultured in MM (FIG. 6f,g). Processes that were consistently enhanced between the two data sets included RNA processing/regulation of RNA metabolic process and regulation of transcription/chromosome organization (FIG. 6f,g). Interestingly, "oxidation-reduction", "fatty acid oxidation" and "cellular response to DNA damage stimulus" were only up-regulated in the proteomic data set (FIG. 6f,g). These biological processes are highly indicative of mammalian postnatal maturation of cardiomyocytes in vivo (5, 28, 29), which additionally highlights the importance of performing proteomic analyses in addition to transcriptomics. Consistent with postnatal maturation, the GO-term "cell cycle regulation" was reduced by MM specifically in the RNA-seq data set, likely due to the low abundance of proteins involved in the cell cycle even in CTRL medium (FIG. 6f,g). The GO-term "heart development" was also up-regulated in hCOs cultured in MM in the RNA-seq data set (FIG. 6f), and key factors involved in cardiac maturation in this GO-term (MYH7, IRX4 and MYBPC3) were also up-regulated in the proteomics analysis (FIG. 6h,i). MYH7 is known to increase during human heart maturation (30), IRX4 nuclear translocation increases during postnatal cardiac maturation (31) and is critical for maintaining cardiac function (32), and cardiomyocytes undergo an additional round of division prior to postnatal cell cycle arrest in MYBPC3 knockout mice (33). We also validated that sarcomeric isoforms known to switch/increase during maturation (24), such as TTN N2B,MYH7/6 and TNNI3/1, increased in hCO cultured in MM using qPCR (FIG. 8g). Collectively, these results demonstrate that hCO cultured in MM undergo multiple postnatal maturation processes including induction of cardiac developmental factors, metabolic switching, DNA damage and a reduction in cell cycle activity. However, our findings also highlight that hCO culture in MM specifically matures these processes, whilst other structural and functional properties associated with maturation are not further enhanced by culture in MM (as found in FIG. 4,5,6,7).

MM Induces a Metabolic Switch from Glycolysis to Fatty Acid Oxidation

Our RNA-seq and proteomics analysis (FIG. 6) revealed that hCO culture in MM represses many glycolysis components and activates many fatty acid oxidation components in hCO (FIG. 9). We next profiled metabolism of hCOs using the Seahorse XF Bioanalyzer mitochondrial stress test with an additional step to measure endogenous fatty acid oxidation using etomoxir (FIG. 10a). In support of a switch to fatty acid oxidation, hCOs from MM had a higher maximal OCR (FIG. 10b), OCR reserve (FIG. 10c) and, increased fatty acid oxidation (FIG. 10d) under the Seahorse test conditions. These changes in oxidative capacity were associated with an increase in mitochondrial content (mtDNA) (FIG. 10e). As ATP uncoupling using carbonyl cyanide-4 (trifluoromethoxy) phenylhydrazone (FCCP) can lead to large increases in extracellular acidification rate (ECAR) in mature cardiomyocytes even in the absence of glucose (34), we chose to use metabolomics to further profile glycolytic and branching pathway metabolic flux in hCO under CTRL medium and MM conditions. Metabolites in the glycolysis pathway, as well as pathways branching from it including hexosamine, pentose phosphate and glycogen pathways were all reduced in MM compared to CTRL medium (FIG. 10f). Together our RNA-seq, proteomics, Seahorse data and metabolomics confirm a switch in metabolism from glycolysis to fatty acid oxidation.

MM Inhibits Cell Cycle and is Associated with Repression of β-Catenin and Induction of the DNA Damage Response (DDR)

We firstly confirmed MM induces a decrease in Ki-67 intensity in multiple hPSC cell lines (H9 and hiPSC, FIG. 12a,b). Additionally, we confirmed our initial whole-mount fluorescence intensity screening data (FIG. 1k) using high-resolution confocal microscopy staining and quantification of hPSC-CM cell cycle activity. We found that hCO culture in MM caused a reduction in percentage of hPSC-CMs in the cell cycle using the general cell cycle marker, Ki-67 (FIG. 11a), and the mitosis specific marker, pH3 (FIG. 11b). hPSC-CM proliferation was markedly reduced in hCOs cultured in MM, with very low overall rates of hPSC-CM mitosis (~0.2% pH3$^+$ hPSC-CMs), which is similar to the postnatal human heart (35).

Figure 11:
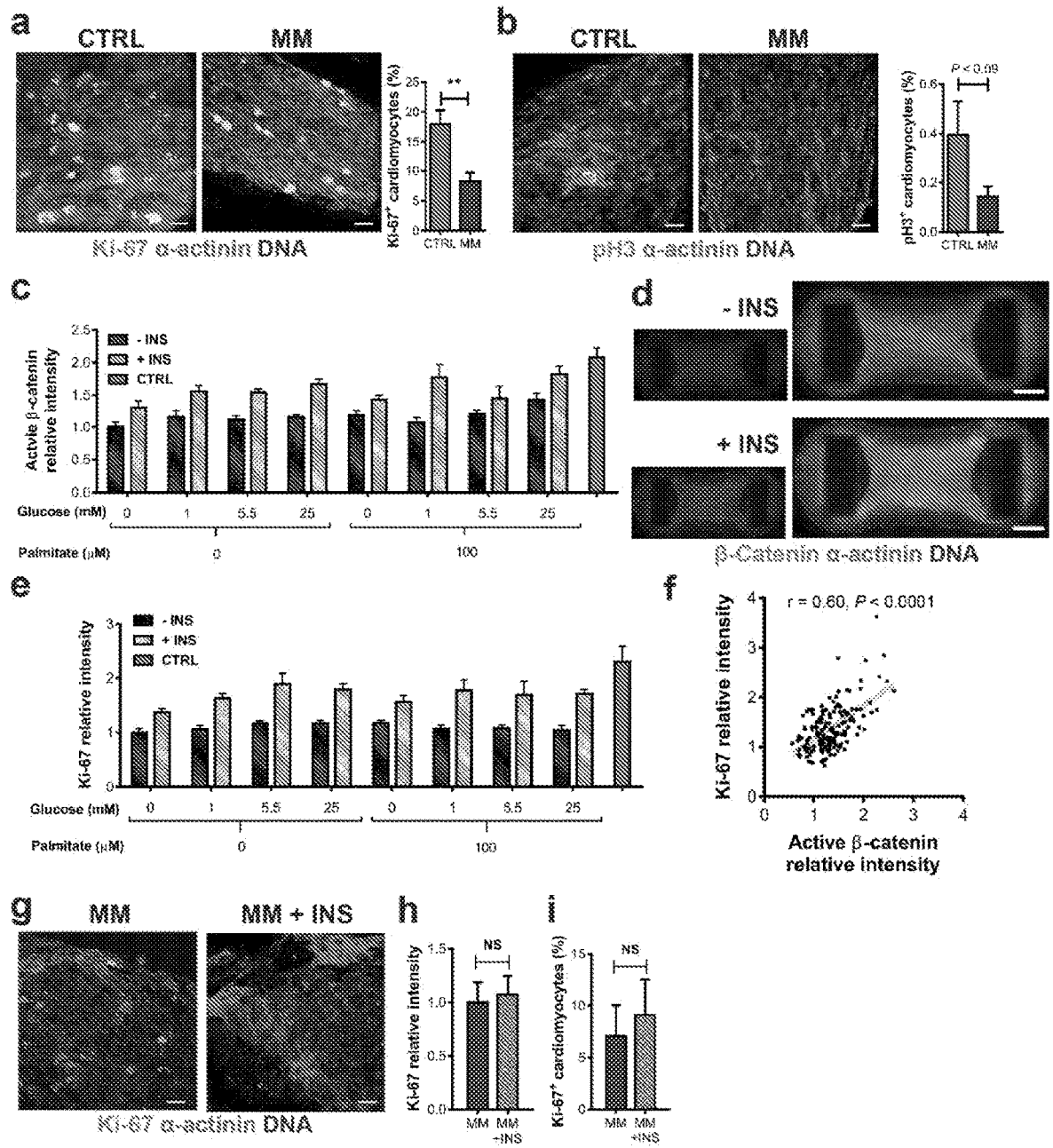

We next wanted to assess how metabolic substrates influenced the cardiac cell cycle. We performed a factorial experiment with glucose, insulin and palmitate following the hCO formation phase. Importantly, all conditions had a similar force of contraction during the first 48 h of culture (FIG. 12c), indicating that the hCOs have similar functional properties and viability at this early stage, even in the absence of glucose and palmitate (in contrast to longer term cultures, FIG. 1i). In these studies, we specifically examined the Wnt/β-catenin signalling pathway, as we have previously identified CHIR99021 (16) as one of the most potent activators of human cardiomyocyte proliferation and have also found this pathway to be transcriptionally repressed during postnatal maturation (5). As a read-out of β-catenin activity in our screen, we performed quantification of activated β-catenin using an antibody that only binds to activated, nuclear-localized β-catenin (36). Activated β-catenin was highly dependent on insulin regardless of the presence of either glucose or palmitate (FIG. 11c,d), as was proliferation (FIG. 11e), and there was a highly significant correlation between activated β-catenin and Ki-67 intensity (FIG. 11f over all hCOs in all conditions). Despite this dependence on insulin signaling for proliferation 2 days after culture in MM, the addition of insulin after 11 days in MM was not sufficient to re-activate hP SC-CM proliferation (FIG. 11g, h,i). This indicates that longer term culture in MM induces desensitization of hPSC-CMs to the proliferative actions of insulin.

The highly oxidative postnatal environment in cardiomyocytes in vivo induces a DDR, which has been proposed as a central mechanism driving cardiomyocyte terminal differentiation (29). Consistent with these findings in vivo, we also found that there was increased expression of DDR proteins in hCO cultured in MM (FIG. 6g, FIG. 13a). There was evidence for induction of the DDR in hCO cultured in MM including increased expression of a marker of oxidative base modification in DNA 8-oxo-7,8-dihydroguanine (8-OxoG) (FIG. 13b) and increased Ser1987 phosphorylated ATM (pATM) (FIG. 13c). Therefore, consistent with in vivo postnatal maturation, the DDR is also associated with proliferative arrest in hCO cultured in MM.

Further Uses of Mature Cardiomyocytes and Organoids

Organoids produced according to the invention will allow more reliable insights into cardiac biology, disease modelling, and toxicology.

Cardiomyocytes in hCO produced in maturation medium (MM) display a reduced level of proliferation compared to other 2D and 3D cardiomyocytes (FIG. 16 a,b). In addition, the cardiomyocytes in hCO cultured in MM are refractory to mitogenic stimulation, the example in this case CHIR99021 (a GSK3 inhibitor) (FIG. 16 a,b). This is consistent with in vivo post-natal cardiac maturation where adult cardiomyocytes no longer enter the cell cycle in response to mitogenic stimulation.

hCO produced in MM can be used to model drug toxicologies as they express the critical ion channels, calcium handling proteins and contractile proteins for a contraction cycle (FIG. 17a). hCO produced in MM accurately predicted high, medium or low risk compounds that interact with the human ether-a-go-go channel (hERG), based on relaxation time prolongation (FIG. 17b,c,d).

The metabolic maturity of hCO produced in MM now enables metabolic diseases to be modelled in hCO. hCO cultured in conditions of diabetes (low insulin, high glucose) exhibit consistent forces of contraction, but increased relaxation times (FIG. 18a,b). This "diastolic dysfunction" is consistent with the functional changes that occur in patients Heart Failure with preserved Ejection Fraction (HFpEF). Therefore, hCO produce in MM may be critical for modelling the effects of metabolic disorders on heart function, and it is known that patients with diabetes have a greater risk of developing cardiomyopathy and HFpEF.

Some genetic diseases can be modelled in 2D cultures but any relating to mature sarcomeric isoforms or ECM require 3D organoids. ALPK3 deficient mature cardiomyocytes can result in cardiomyopathy show reduced contraction force compared to normal cardiomyocytes. Similarly, a reduced contraction force may be measured in NKX2-5 deficient cardiomyocytes. Analysis of the effect of mutant genes such as these will be undertaken in mature cardiomyocytes and/or organoids that have been produced using the maturation medium disclosed herein.

Further Uses of Maturation Medium

Many applications may require the culture of 2D cardiomyocytes rather than culture in hCO. To determine whether the MM can also work in 2D we have compared different medium compositions and their capacity to reduce cell cycle activity (FIG. 19). We found that the same MM or MM with the B27 replaced with human serum albumin was sufficient to reduce cell cycle activity also in 2D culture even over short time-frames.

Discussion hPSC-CMs have become widely used to study human cardiac biology, development, and physiology. However, they are typically immature, which limits their capacity to accurately model adult cardiac biology. While engineered heart muscle can improve hPSC-CM maturation in terms of structure and function (10, 14), the key upstream drivers of metabolic maturation and cell cycle arrest are largely unknown.

In order to identify central regulators of hPSC-CM maturation and cell cycle exit, we developed a miniaturized semi-automated cardiac organoid culture platform (Heart-Dyno) to facilitate screening. Through systematic and iterative screening we were able to demonstrate that distinct physiological hallmarks of the maturation process were driven by different cues. For example, we found that maturation of many parameters such as the structural, electrophysiological, calcium handling, as well as responses to adrenergic stimulation, were supported by the 3D engineered heart tissue environment. These parameters in our hCO were similar to those reported using other cardiac tissue engineering platforms (8-12). However, we found that switching metabolism to fatty acid oxidation was a key driver not only for shifting the expression of metabolism genes, mitochondrial biogenesis and fatty acid oxidation, but also for increased expression of adult sarcomeric protein isoforms and cell cycle exit. Therefore, different aspects of the adult cardiomyocyte phenotype are governed by distinct cues, which need to be carefully controlled for the generation of mature hPSC-CMs.

During the first week of the postnatal period in vivo a metabolic switch to fatty acid oxidation and cell cycle exit occurs in the heart, in concert with a change in serum composition from glycolytic substrates to fatty acids (4). In this study, we found that mimicking these changes in metabolic substrate provision is a major driver of not only the metabolic maturation, but also the transcriptional and cell cycle maturation in human cardiomyocytes. Specifically, we found that a switch from commonly used high insulin, carbohydrate-based medium to a low carbohydrate, low insulin, palmitate-based medium enhanced the maturation of hCOs. These maturation conditions are in contrast to the typical cell growth environments, which generally comprise glucose, insulin and serum and are designed to increase cellular proliferation. Altering the metabolic environment was critical to promote maturation in hCO and may also represent a viable approach for promoting differentiation and functional maturation of other cell types.

Recent studies have suggested that oxygen tension is linked to cardiomyocyte proliferation (28, 29, 49) and revealed that a high oxygen environment is a key trigger for postnatal cardiomyocyte cell cycle exit (29). However, the in vitro culture of hPSC-CMs at atmospheric oxygen (~21% $O_2$) is not sufficient to drive cell cycle exit (16, 50). Our study demonstrates that a switch to fatty acid oxidation via alteration of metabolic substrate utilization, in a high oxygen environment, is a driver of hPSC-CM cell-cycle arrest. This suggests that the high oxygen environment works in concert with changes in metabolic substrate availability after birth to govern cardiomyocyte cell cycle arrest. This is also supported in vivo by a recent study demonstrating a link between reduced oxygen concentrations and reactivation of cardiomyocyte proliferation and cardiac regeneration in the adult heart, which was associated with a metabolic switch to glycolysis (28). Together, these studies establish a causal link between postnatal metabolic adaptations, oxygen tension and cardiomyocyte proliferation.

Our findings show that switching hPSC-CM metabolism to fatty acid oxidation induces long-lasting changes in β-catenin and YAP1 signalling, as well as the DDR, which results in hPSC-CM cell cycle withdrawal. Cooperativity between β-catenin and YAP signalling has been reported in the embryonic heart where they interact to control cardiomyocyte proliferation during heart development (41). Moreover, Hippo/Yap signalling has emerged as a central regulator of cardiac regenerative capacity in the neonatal period (51, 52). Our study suggests that postnatal alterations in cardiomyocyte metabolism could operate as a key switch leading to cardiomyocyte cell cycle shut down via repression of β-catenin and YAP signalling after birth. Similarly, alterations in metabolism are known to influence β-catenin and YAP activity in other cell types (53, 54). Therefore, these findings support a model whereby β-catenin, YAP1, metabolism and the DDR are intimately linked and cooperate to regulate the cardiac cell cycle and maturation.

The production of human organoids has rapidly advanced over the past few years. Coupled with higher throughput screening platforms, such as the Heart-Dyno, organoid experiments have the potential to rapidly expand our knowledge of human biology and potentially unlock novel therapeutic strategies for many diseases.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

TABLE 1

Antibodies used in this study.

| Antibody | Species | Company | Cat No | Dilution |
|---|---|---|---|---|
| α-actinin (clone EA-53) | Mouse IgG$_1$ | Sigma | A7811 | 1:1000 |
| Ki-67 (D3B5) | Rabbit IgG | Cell Signaling Technology | 9129 | 1:400 |
| Anti-phospho-Histone H3 (Ser10) (pH 3) | Rabbit Polyclonal | Millipore | 06-570 | 1:200 |
| Active β-catenin (PY489) | Mouse IgM | Developmental Studies Hybridoma Bank | PY489-B-catenin | 5 μg/ml |
| Titin | Mouse IgM | Developmental Studies Hybridoma Bank | 9 D10 | 5 μg/ml |
| MLC2V | Rabbit IgG | Protein Tech Group | 10906-1-AP | 1:200 |
| CD31 | Mouse IgG$_1$ | Dako | M082329-2 | 1:200 |
| CD90 | Mouse IgG$_{2A}$ | RnD Systems | MAB2067 | 1:200 (after reconstitution using manufacterer's guidelines) |
| WT-1 | Rabbit IgG | Abcam | AB89901 | 1:200 |
| Caveolin 3 | Mouse IgG$_1$ | BD Transduction Laboratories | 610421 | 1:200 |
| pATM | Mouse IgG$_1$ | Santa Cruz Biotechnology | sc-47739 | 1:100 |
| 8-oxoG | Mouse IgM | Abcam | Ab206461 | 1:100 |
| pan-cadherin | Rabbit anti-serum | Sigma | C3678 | 1:200 |
| Connexin 43 (Cx43) | Rabbit IgG | Abcam | ab11370 | 1:200 |
| GFP | Chicken Polyclonal | Abcam | Ab13970 | 1:200 |
| Alexa Fluor ® 488 goat anti-Rabbit IgG (H + L) | NA | Life Technologies | A-11034 | 1:400 |
| Alexa Fluor ® 488 Goat anti-Mouse IgG (H + L) | NA | Life Technologies | A-11029 | 1:400 |
| Alexa Fluor ® 488 Goat Anti-Mouse IgM (μ chain) | NA | Life Technologies | A-21042 | 1:400 |
| Alexa Fluor ® 555 goat anti-Rabbit IgG (H + L) | NA | Life Technologies | A-21428 | 1:400 |
| Alexa Fluor ® 555 Goat Anti-Mouse IgG (H + L) | NA | Life Technologies | A-21422 | 1:400 |
| Alexa Fluor ® 633 Goat Anti-Rabbit IgG (H + L) | NA | Life Technologies | A-21070 | 1:400 |
| Alexa Fluor ® 488 goat anti-chicken IgG (H + L) | NA | Life Technologies | A-11039 | 1:400 |

TABLE 2 qPCR primers used in this study.

| Gene | F | R | Size (bp) | Acc No |
|---|---|---|---|---|
| RNA18S5 | GCTGAGAAGACGGTCGAACT (SEQ ID NO: 1) | CGCAGGTTCACCTACGGAAA (SEQ ID NO: 2) | 74 | NR_003286.2 |
| αMHC (MYH6) | CTCCTCCTACGCAACTGCCG (SEQ ID NO: 3) | CGACACCGTCTGGAAGGATGA (SEQ ID NO: 4) | 85 | NM_002471 |
| βMHC (MYH7) | GACCAGATGAATGAGCACCG (SEQ ID NO: 5) | GGTGAGGTCGTTGACAGAACG (SEQ ID NO: 6) | 63 | NM_000257 |
| MLC2α (MYL7) | CAGCGGCAAAGGGGTGGTAAC (SEQ ID NO: 7) | GGTCCATGGGTGTCAGGGCGAA (SEQ ID NO: 8) | 113 | NM_021223.2 |
| MLC2v (MYL2) | GGCGCCAACTCCAACGTGTT (SEQ ID NO: 9) | ACGTTCACTCGCCCAAGGGC (SEQ ID NO: 10) | 149 | NM_000432.3 |

TABLE 2-continued qPCR primers used in this study.

| Gene | F | R | Size (bp) | Acc No |
|---|---|---|---|---|
| TTN ALL (Ex49-50) | GTAAAAAGAGCTGCCCCAGTGA (SEQ ID NO: 11) | GCTAGGTGGCCCAGTGCTACT (SEQ ID NO: 12) | 68 | NM_001267550.1 NM_001256850.1 NM_133437.3 NM_133432.3 NM_003319.4 |
| TTN N2B (Ex50-219) | CCAATGAGTATGGCAGTGTCA (SEQ ID NO: 13) | TACGTTCCGGAAGTAATTTGC (SEQ ID NO:14) | 93 | NM_133437.3 NM_133432.3 NM_003319.4 |
| cTNNI (TNNI3) | CCTCCAACTACCGCGCTTAT (SEQ ID NO: 15) | CTGCAATTTTCTCGAGGCGG (SEQ ID NO: 16) | 77 | NM_000363.4 |
| ssTNNI (TNNI1) | GCTCCACGAGGACTGAACAA (SEQ ID NO: 17) | CTTCAGCAAGAGTTTGCGGG (SEQ ID NO: 18) | 97 | NM_003281.3 |
| ND1 (mitochondrial DNA) | AACCTCAACCTAGGCCTCCT (SEQ ID NO: 19) | GAGTTTGATGCTCACCCTGA (SEQ ID NO: 20) | 86 | NC_012920.1 |
| BIRC5 | TTCTCAAGGACCACCGCATC (SEQ ID NO: 21) | CCAAGTCTGGCTCGTTCTCA (SEQ ID NO: 22) | 126 | NM_001012271.1 NM_001168.2 NM_001012270.1 |

REFERENCES

1. Porrello E R & Olson E N (2014) A neonatal blueprint for cardiac regeneration. Stem cell research 13(3 Pt B):556-570.
2. Porrello E R, et al. (2013) Regulation of neonatal and adult mammalian heart regeneration by the miR-15 family. Proc Natl Acad Sci USA 110(1):187-192.
3. Porrello E R, et al. (2011) Transient regenerative potential of the neonatal mouse heart. Science 331(6020): 1078-1080.
4. Girard J, Ferre P, Pegorier J P, & Duee P H (1992) Adaptations of glucose and fatty acid metabolism during perinatal period and suckling-weaning transition. Physiological reviews 72(2):507-562.
5. Sim C B, et al. (2014) Dynamic changes in the cardiac methylome during postnatal development. FASEB J 29(4): 1329-1343.
6. Shekhawat P S, Matern D, & Strauss A W (2005) Fetal fatty acid oxidation disorders, their effect on maternal health and neonatal outcome: impact of expanded newborn screening on their diagnosis and management. Pediatric research 57(5 Pt 2):78R-86R.
7. Tiburcy M & Zimmermann W H (2014) Modeling myocardial growth and hypertrophy in engineered heart muscle. Trends Cardiovasc Med 24(1):7-13.
8. Boudou T, et al. (2012) A microfabricated platform to measure and manipulate the mechanics of engineered cardiac microtissues. Tissue Eng Part A 18(9-10):910-919.
9. Tulloch N L, et al. (2011) Growth of engineered human myocardium with mechanical loading and vascular coculture. Circ Res 109(1):47-59.
10. Zhang D, et al. (2013) Tissue-engineered cardiac patch for advanced functional maturation of human ESC-derived cardiomyocytes. Biomaterials 34(23):5813-5820.
11. Schaaf S, et al. (2011) Human engineered heart tissue as a versatile tool in basic research and preclinical toxicology. PLoS ONE 6(10):20.
12. Nunes S S, et al. (2013) Biowire: a platform for maturation of human pluripotent stem cell-derived cardiomyocytes. Nat Methods 10(8):781-787.
13. Voges H K, et al. (2017) Development of a human cardiac organoid injury model reveals innate regenerative potential. Development 144(6):1118-1127.
14. Tiburcy M, et al. (2017) Defined Engineered Human Myocardium with Advanced Maturation for Applications in Heart Failure Modelling and Repair. Circulation 135 (19): 1832-1847.
15. Zimmermann W H, et al. (2006) Engineered heart tissue grafts improve systolic and diastolic function in infarcted rat hearts. Nature medicine 12(4):452-458.
16. Titmarsh D M, et al. (2016) Induction of Human iPSC-Derived Cardiomyocyte Proliferation Revealed by Combinatorial Screening in High Density Microbioreactor Arrays. Scientific reports 6:24637.
17. Bougneres P F, Karl I E, Hillman L S, & Bier D M (1982) Lipid transport in the human newborn. Palmitate and glycerol turnover and the contribution of glycerol to neonatal hepatic glucose output. J Clin Invest 70(2):262-270.
18. Tiburcy M, et al. (2011) Terminal differentiation, advanced organotypic maturation, and modeling of hypertrophic growth in engineered heart tissue. Circ Res 109 (10):1105-1114.
19. Desbois-Mouthon C, et al. (2001) Insulin and IGF-1 stimulate the beta-catenin pathway through two signalling cascades involving GSK-3beta inhibition and Ras activation. Oncogene 20(2):252-259.
20. Racca A W, et al. (2016) Contractile properties of developing human fetal cardiac muscle. J Physiol 594(2): 437-452.
21. Moreo A, et al. (2009) Influence of myocardial fibrosis on left ventricular diastolic function: noninvasive assessment by cardiac magnetic resonance and echo. Circulation. Cardiovascular imaging 2(6):437-443.
22. Zimmermann W H, et al. (2002) Tissue engineering of a differentiated cardiac muscle construct. Circ Res 90(2): 223-230.

23. Eder A, Vollert I, Hansen A, & Eschenhagen T (2016) Human engineered heart tissue as a model system for drug testing. *Advanced Drug Delivery Reviews* 96:214-224.
24. Yang X, Pabon L, & Murry C E (2014) Engineering adolescence: maturation of human pluripotent stem cell-derived cardiomyocytes. *Circ Res* 114(3):511-523.
25. Kuppusamy K T, et al. (2015) Let-7 family of microRNA is required for maturation and adult-like metabolism in stem cell-derived cardiomyocytes. *Proc Natl Acad Sci USA* 112(21):E2785-2794.
26. Pinto A R, et al. (2016) Revisiting Cardiac Cellular Composition. *Circ Res* 118(3):400-409.
27. DeLaughter D M, et al. (2016) Single-Cell Resolution of Temporal Gene Expression during Heart Development. *Dev Cell* 39(4):480-490.
28. Nakada Y, et al. (2016) Hypoxia induces heart regeneration in adult mice. *Nature* 541(7636):222-227.
29. Puente B N, et al. (2014) The oxygen-rich postnatal environment induces cardiomyocyte cell-cycle arrest through DNA damage response. *Cell* 157(3):565-579.
30. Dubois N C, et al. (2011) SIRPA is a specific cell-surface marker for isolating cardiomyocytes derived from human pluripotent stem cells. *Nat Biotechnol* 29(11):1011-1018.
31. Nelson D O, Jin D, Downs K, Kamp T J, & Lyons G E (2014) Irx4 identifies a chamber-specific cell population that contributes to ventricular myocardium development. *Developmental dynamics: an official publication of the American Association of Anatomists* 243(3):381-392.
32. Bruneau B G, et al. (2001) Cardiomyopathy in Irx4-Deficient Mice Is Preceded by Abnormal Ventricular Gene Expression. *Molecular and Cellular Biology* 21(5): 1730-1736.
33. Jiang J, et al. (2015) Cardiac myosin binding protein C regulates postnatal myocyte cytokinesis. *Proceedings of the National Academy of Sciences of the United States of America* 112(29):9046-9051.
34. Readnower R D, Brainard R E, Hill B G, & Jones S P (2012) Standardized bioenergetic profiling of adult mouse cardiomyocytes. *Physiological genomics* 44(24): 1208-1213.
35. Polizzotti B D, et al. (2015) Neuregulin stimulation of cardiomyocyte regeneration in mice and human myocardium reveals a therapeutic window. *Science translational medicine* 7(281):281ra245.
36. Sturzu A C, et al. (2015) Fetal Mammalian Heart Generates a Robust Compensatory Response to Cell Loss. *Circulation* 132(2):109-121.
37. Eulalio A, et al. (2012) Functional screening identifies miRNAs inducing cardiac regeneration. *Nature* 492 (7429):376-381.
38. Xin M, et al. (2013) Hippo pathway effector Yap promotes cardiac regeneration. *Proceedings of the National Academy of Sciences* 110(34): 13839-13844.
39. Zhao Y Y, et al. (1998) Neuregulins promote survival and growth of cardiac myocytes. Persistence of ErbB2 and ErbB4 expression in neonatal and adult ventricular myocytes. *The Journal of biological chemistry* 273 (17): 10261-10269.
40. Rosenbluh J, et al. (2012) beta-Catenin-driven cancers require a YAP1 transcriptional complex for survival and tumorigenesis. *Cell* 151(7):1457-1473.
41. Heallen T, et al. (2011) Hippo pathway inhibits Wnt signaling to restrain cardiomyocyte proliferation and heart size. *Science* 332(6028):458-461.
42. Xin M, et al. (2011) Regulation of insulin-like growth factor signaling by Yap governs cardiomyocyte proliferation and embryonic heart size. *Science signaling* 4(196): ra70.
43. Tao G, et al. (2016) Pitx2 promotes heart repair by activating the antioxidant response after cardiac injury. *Nature* 534(7605):119-123.
44. Zanconato F, et al. (2015) Genome-wide association between YAP/TAZ/TEAD and AP-1 at enhancers drives oncogenic growth. *Nature cell biology* 17(9):1218-1227.
45. Jin F, et al. (2013) A high-resolution map of the three-dimensional chromatin interactome in human cells. *Nature* 503(7475):290-294.
46. Augeri D J, et al. (2012) Mst1 kinase inhibitors and methods of their use. *Patent* WO/2012/121992.
47. Clevers H (2006) Wnt/beta-catenin signaling in development and disease. *Cell* 127(3):469-480.
48. Xu C M, et al. (2013) Mst1 overexpression inhibited the growth of human non-small cell lung cancer in vitro and in vivo. *Cancer gene therapy* 20(8):453-460.
49. Kimura W, et al. (2015) Hypoxia fate mapping identifies cycling cardiomyocytes in the adult heart. *Nature* 523 (7559):226-230.
50. Burridge P W, et al. (2014) Chemically defined generation of human cardiomyocytes. *Nat Methods* 11(8):855-860.
51. Xin M, et al. (2013) Hippo pathway effector Yap promotes cardiac regeneration. *Proc Natl Acad Sci USA* 110(34):13839-13844.
52. Morikawa Y, et al. (2015) Actin cytoskeletal remodeling with protrusion formation is essential for heart regeneration in Hippo-deficient mice. *Science signaling* 8(375): ra41.
53. Wang W, et al. (2015) AMPK modulates Hippo pathway activity to regulate energy homeostasis. *Nature cell biology* 17(4):490-499.
54. Chocarro-Calvo A, Garcia-Martinez J M, Ardila-Gonzalez S, De la Vieja A, & Garcia-Jimenez C (2013) Glucose-induced beta-catenin acetylation enhances Wnt signaling in cancer. *Molecular cell* 49(3):474-486.
55. Rohrig F & Schulze A (2016) The multifaceted roles of fatty acid synthesis in cancer. *Nature reviews. Cancer* 16(11):732-749.
56. Hudson J, Titmarsh D, Hidalgo A, Wolvetang E, & Cooper-White J (2012) Primitive cardiac cells from human embryonic stem cells. *Stem Cells Dev* 21(9):1513-1523.
57. Voges H K, et al. (2017) Development of a Human Cardiac Organoid Injury Model Reveals Innate Regenerative Potential. *Development In Press*.
58. Zimmermann W-H, Hudson J E, & Tiburcy M (2015) A method to direct differentiation of pluripotent stem cells into functional heart muscle *Patent* WO 2015/040142 A1.

The invention claimed is:

1. A cardiac cell maturation medium comprising a base medium, one or more fatty acids, glucose and albumin,
   wherein the one or more fatty acids include palmitate,
   wherein glucose is present at a concentration of 0.5 mM to 5.5 mM,
   wherein the one or more fatty acids are present at a concentration of about 10 μM to about 200 μM,
   and wherein the maturation medium does not comprise insulin.

2. The cardiac cell maturation medium of claim 1, which comprises a gelling medium.

3. The cardiac cell maturation medium of claim 2, which comprises one or more extracellular matrix (ECM) molecules or components thereof.

4. The cardiac cell maturation medium of claim 1, wherein the one or more fatty acids and glucose are present at a concentration ratio of about 1:10 M.

5. The cardiac cell maturation medium of claim 1 comprising more than one $C_{12}$-$C_{20}$ saturated fatty acid.

6. The cardiac cell maturation medium of claim 1, which does not comprise TGF, or comprises minimal TGF.

7. A cardiac cell culture system comprising:
   (i) cardiac cell maturation medium of claim 1; and
   (ii) a cardiac cell culture vessel comprising a plurality of wells that each comprise opposed poles that extend substantially perpendicularly from a basal surface of the well.

8. The cardiac cell culture system of claim 7, wherein displacement of the opposed poles caused by muscle bundles in the well facilitates contractile force measurements.

9. The cardiac cell culture system of claim 8, which is, or is a component of, a heart dynamometer.

10. A method of culturing cardiac cells, the method including contacting one or more cardiomyocytes with the cardiac cell maturation medium of claim 1 for sufficient time and under suitable conditions to induce or promote maturation of one or a plurality of cardiomyocytes.

11. The method of claim 10, wherein the one or more cardiomyocytes are initially gelled in the presence of the ECM components or molecules and albumin.

12. The method of claim 11, wherein the glucose and one or more fatty acids are subsequently added to the gelled cardiomyocytes in the absence of insulin.

13. The method of claim 10, wherein the one or more cardiomyocytes have been differentiated from one or more progenitor cells.

14. A method of identifying one or more molecules that modulate cardiac cell maturation, the method including:
    contacting one or more cardiomyocytes with one or more candidate molecules in the cell culture system of claim 7,
    whereby modification of the maturation of one or a plurality of the cardiomyocytes indicates that the candidate molecule is a modulator of cardiac cell maturation.

15. A method of determining, assessing or monitoring the effect of one or more molecules upon a cardiac cell, tissue or organoid, the method including:
    producing a cardiac cell, organoid or engineered heart tissue according to the method of claim 10;
    contacting the cardiac cell, organoid or engineered heart tissue with the one or more molecules; and
    determining, assessing or monitoring the effect of the one or more molecules upon the cardiac cell, organoid or engineered heart tissue.

16. A method of culturing cardiac cells, the method including culturing the one or more cardiomyocytes in the cell culture system of claim 7 so as to contact the one or more cardiomyocytes with the cardiac cell maturation medium for sufficient time and under suitable conditions to induce or promote maturation of one or a plurality of cardiomyocytes.

17. The cardiac cell maturation medium of claim 3, wherein the ECM molecules are present at a concentration of 7-12% (v/v) of gelling medium.

18. The cardiac cell maturation medium of claim 1, wherein glucose is present at a concentration of about 1 mM.

19. The cardiac cell maturation medium of claim 1, wherein the one or more fatty acids are present at a concentration of about 100 μM.

* * * * *

SEQUENCE LISTING

<160> NUMBER OF SEQ ID NOS: 22

<210> SEQ ID NO 1
<211> LENGTH: 20

```
<212> TYPE: DNA
<213> ORGANISM: Homo sapiens

<400> SEQUENCE: 1
gctgagaaga cggtcgaact                                              20

<210> SEQ ID NO 2
<211> LENGTH: 20
<212> TYPE: DNA
<213> ORGANISM: Homo sapiens

<400> SEQUENCE: 2
cgcaggttca cctacggaaa                                              20

<210> SEQ ID NO 3
<211> LENGTH: 20
<212> TYPE: DNA
<213> ORGANISM: Homo sapiens

<400> SEQUENCE: 3
ctcctcctac gcaactgccg                                              20

<210> SEQ ID NO 4
<211> LENGTH: 21
<212> TYPE: DNA
<213> ORGANISM: Homo sapiens

<400> SEQUENCE: 4
cgacaccgtc tggaaggatg a                                            21

<210> SEQ ID NO 5
<211> LENGTH: 20
<212> TYPE: DNA
<213> ORGANISM: Homo sapiens

<400> SEQUENCE: 5
gaccagatga atgagcaccg                                              20

<210> SEQ ID NO 6
<211> LENGTH: 21
<212> TYPE: DNA
<213> ORGANISM: Homo sapiens

<400> SEQUENCE: 6
ggtgaggtcg ttgacagaac g                                            21

<210> SEQ ID NO 7
<211> LENGTH: 22
<212> TYPE: DNA
<213> ORGANISM: Homo sapiens

<400> SEQUENCE: 7
cagcggcaaa ggggtggtga ac                                           22

<210> SEQ ID NO 8
<211> LENGTH: 22
<212> TYPE: DNA
<213> ORGANISM: Homo sapiens

<400> SEQUENCE: 8
ggtccatggg tgtcagggcg aa                                           22

<210> SEQ ID NO 9
```

```
<210> SEQ ID NO 9
<211> LENGTH: 20
<212> TYPE: DNA
<213> ORGANISM: Homo sapiens

<400> SEQUENCE: 9
ggcgccaact ccaacgtgtt                                               20

<210> SEQ ID NO 10
<211> LENGTH: 20
<212> TYPE: DNA
<213> ORGANISM: Homo sapiens

<400> SEQUENCE: 10
acgttcactc gcccaagggc                                               20

<210> SEQ ID NO 11
<211> LENGTH: 22
<212> TYPE: DNA
<213> ORGANISM: Homo sapiens

<400> SEQUENCE: 11
gtaaaaagag ctgccccagt ga                                            22

<210> SEQ ID NO 12
<211> LENGTH: 21
<212> TYPE: DNA
<213> ORGANISM: Homo sapiens

<400> SEQUENCE: 12
gctaggtggc ccagtgctac t                                             21

<210> SEQ ID NO 13
<211> LENGTH: 21
<212> TYPE: DNA
<213> ORGANISM: Homo sapiens

<400> SEQUENCE: 13
ccaatgagta tggcagtgtc a                                             21

<210> SEQ ID NO 14
<211> LENGTH: 21
<212> TYPE: DNA
<213> ORGANISM: Homo sapiens

<400> SEQUENCE: 14
tacgttccgg aagtaatttg c                                             21

<210> SEQ ID NO 15
<211> LENGTH: 20
<212> TYPE: DNA
<213> ORGANISM: Homo sapiens

<400> SEQUENCE: 15
cctccaacta ccgcgcttat                                               20

<210> SEQ ID NO 16
<211> LENGTH: 20
<212> TYPE: DNA
<213> ORGANISM: Homo sapiens

<400> SEQUENCE: 16
ctgcaatttt ctcgaggcgg                                               20
```

```
<210> SEQ ID NO 17
<211> LENGTH: 20
<212> TYPE: DNA
<213> ORGANISM: Homo sapiens

<400> SEQUENCE: 17
gctccacgag gactgaacaa                                                20

<210> SEQ ID NO 18
<211> LENGTH: 20
<212> TYPE: DNA
<213> ORGANISM: Homo sapiens

<400> SEQUENCE: 18
cttcagcaag agtttgcggg                                                20

<210> SEQ ID NO 19
<211> LENGTH: 20
<212> TYPE: DNA
<213> ORGANISM: Homo sapiens

<400> SEQUENCE: 19
aacctcaacc taggcctcct                                                20

<210> SEQ ID NO 20
<211> LENGTH: 20
<212> TYPE: DNA
<213> ORGANISM: Homo sapiens

<400> SEQUENCE: 20
gagtttgatg ctcaccctga                                                20

<210> SEQ ID NO 21
<211> LENGTH: 20
<212> TYPE: DNA
<213> ORGANISM: Homo sapiens

<400> SEQUENCE: 21
ttctcaagga ccaccgcatc                                                20

<210> SEQ ID NO 22
<211> LENGTH: 20
<212> TYPE: DNA
<213> ORGANISM: Homo sapiens

<400> SEQUENCE: 22
ccaagtctgg ctcgttctca                                                20
```